(12) United States Patent
Leboulch et al.

(10) Patent No.: US 10,105,451 B2
(45) Date of Patent: Oct. 23, 2018

(54) THERAPEUTIC RETROVIRAL VECTORS FOR GENE THERAPY

(71) Applicants: BLUEBIRD BIO, INC., Cambridge, MA (US); MASSACHUSETTS INSTITUTE OF TECHNOLOGY, Cambridge, MA (US)

(72) Inventors: Philippe Louis Leboulch, Bangkok (TH); Robert Pawliuk, Medford, MA (US); Karen Westerman, Reading, MA (US)

(73) Assignees: bluebird bio, Inc., Cambridge, MA (US); Massachusetts Institute of Technology, Cambridge, MA (US)

(*) Notice: Subject to any disclaimer, the term of this patent is extended or adjusted under 35 U.S.C. 154(b) by 0 days.

(21) Appl. No.: 14/700,021

(22) Filed: Apr. 29, 2015

(65) Prior Publication Data

US 2016/0022839 A1 Jan. 28, 2016

Related U.S. Application Data

(60) Division of application No. 13/242,815, filed on Sep. 23, 2011, now Pat. No. 9,068,199, which is a continuation of application No. 12/976,078, filed on Dec. 22, 2010, now abandoned, which is a continuation of application No. 11/150,785, filed on Jun. 9, 2005, now Pat. No. 7,901,671, which is a continuation of application No. PCT/US03/39526, filed on Dec. 11, 2003.

(60) Provisional application No. 60/433,321, filed on Dec. 13, 2002, provisional application No. 60/475,822, filed on Jun. 4, 2003, provisional application No. 60/513,312, filed on Oct. 21, 2003.

(51) Int. Cl.
| | |
|---|---|
| *A01N 63/00* | (2006.01) |
| *C12N 15/00* | (2006.01) |
| *C07H 21/04* | (2006.01) |
| *A61K 48/00* | (2006.01) |
| *A01K 67/027* | (2006.01) |
| *C07K 14/805* | (2006.01) |
| *C12N 15/85* | (2006.01) |
| *C12N 15/86* | (2006.01) |
| *A61K 38/42* | (2006.01) |
| *C12N 15/867* | (2006.01) |
| *C12N 15/63* | (2006.01) |

(52) U.S. Cl.
CPC ...... *A61K 48/0058* (2013.01); *A01K 67/0278* (2013.01); *A61K 38/42* (2013.01); *C07K 14/805* (2013.01); *C12N 15/8509* (2013.01); *C12N 15/86* (2013.01); *A01K 2207/15* (2013.01); *A01K 2217/00* (2013.01); *A01K 2227/105* (2013.01); *A01K 2267/03* (2013.01); *A61K 48/00* (2013.01); *C07H 21/04* (2013.01); *C12N 15/63* (2013.01); *C12N 15/867* (2013.01); *C12N 2510/00* (2013.01); *C12N 2740/15043* (2013.01); *C12N 2740/16011* (2013.01); *C12N 2740/16043* (2013.01); *C12N 2830/008* (2013.01); *C12N 2830/40* (2013.01)

(58) Field of Classification Search
CPC .. C12N 15/63; C12N 15/867; C12N 2510/00; C12N 2740/16011; C12N 2740/16043; C12N 2830/008; C07H 21/04
USPC ........... 424/93.21; 435/320.1, 455; 536/23.5, 536/24.1
See application file for complete search history.

(56) References Cited

U.S. PATENT DOCUMENTS

| | | | |
|---|---|---|---|
| 5,861,488 A | 1/1999 | Leboulch et al. | |
| 6,136,597 A | 10/2000 | Hope et al. | |
| 6,252,048 B1 | 6/2001 | Kelley et al. | |
| 6,395,549 B1 | 5/2002 | Tuan et al. | |
| 7,198,950 B2 | 4/2007 | Trono et al. | |
| 7,901,671 B2 | 3/2011 | Leboulch et al. | |
| 9,068,199 B2 | 6/2015 | Leboulch et al. | |
| 2004/0033604 A1 | 2/2004 | Koblinger et al. | |
| 2004/0241141 A1 | 12/2004 | Pawliuk et al. | |
| 2011/0274669 A1 | 11/2011 | Leboulch et al. | |

FOREIGN PATENT DOCUMENTS

| | | |
|---|---|---|
| EP | 1581056 | 2/2010 |
| WO | WO 94/23046 | 10/1994 |
| WO | WO 00/23606 | 4/2000 |
| WO | WO 02/082908 | 10/2002 |
| WO | WO 02/087341 | 11/2002 |
| WO | WO 04/054512 | 7/2004 |

OTHER PUBLICATIONS

Taha, Masoumeh F., 2010, Current Stem Cell research & therapy, vol. 5, p. 23-36.*
Wu et al., 2012, Ageing Research Reviews, vol. 11, p. 32-40.*
Sharp III et al., 2014, Frontiers in Oncology, vol. 4, Article 299, p. 1-13.*
Li et al., 2009, Transplant Immunology, vol. 21, p. 70-74.*
Sprangers et al., 2008, Kidney International, vol. 74, p. 14-21.*
Bell et al., 2001, Geneseq Accession No. AAF67644, computer printout p. 5-6.
Bell et al.,"The Protein CTCF is Required for the Enhancer Blocking Activity of Vertebrate Insulators," Cell, 98:387-396, 1999.
Castro, et al., 2001 Histl. Histophathol., 16:1225-1238, 2001.
Chattopadhyay et al., *Virus Research*, 99:139-145, 2004.

(Continued)

*Primary Examiner* — Shin Lin Chen
(74) *Attorney, Agent, or Firm* — Cooley LLP

(57) ABSTRACT

The invention provides improved compositions and methods for achieving gene therapy in hematopoietic cells and hematopoietic precursor cells, including erythrocytes, erythroid progenitors, and embryonic stem cells. The invention further provides improved gene therapy methods for treating hematopoietic-related disorders. Retroviral gene therapy vectors that are optimized for erythroid specific expression and treatment of hemoglobinopathic conditions are disclosed.

11 Claims, 17 Drawing Sheets

Specification includes a Sequence Listing.

(56) References Cited

OTHER PUBLICATIONS

Chung et al.,"A 5' Element of the Chicken .beta.-Globin Domain Serves as an Insulator in Human Erythroid Cells and Protects against Position Effect in *Drosphila*," Cell, 74:505-514, 1993.
Chung, et al., "Characterization of the chicken β-globin insulator," Proc. Natl. Aca. Sci. USA, 94:575-580, 1997.
Copreni et al., Gene Therapy, 11:S67-S75, 2004.
Deonarain, Expert Opin. Ther. Pat., 8:53-69, 1998.
Eck et al., *Goodman & Gilman's The Pharmacological Basis of Therapeutics*, McGraw-Hill, New York, p. 77-101, 1996.
European Supplemental Search Report, dated Dec. 19, 2006 for EP Application No. 03813391.4, 7 pages.
Gorecki, *Expert Opin. Emerging Drugs*, 6(2): 187-198, 2001.
Hino et al., "Incorporation of Chromatin Insulator from Sea Urchin Arylsulfatase Gene Into Lentiviral Vector Improves Expression in Myeloid Progenitor Cells," *Gene Transfer—Biology and Marking Studies*, Abstract No. 5522, p. 484b, 2002.
Imren et al. "Correction of Anemia in Beta-Thalassemia Mice Transplanted with Syngeneic Marrow Transduced with Entiviral Vector Encoding Human Beta-Globin Gene," *Blood*, 98(11), Part 1: 692a, 2001.
Imren et al., "Preferred Intragenic Integration with High-Level Erythroid Expression of a Lentiviral Vector Bearing an Anti-Sickling (beta.-Globin Transgene in NOD/SCID Mouse Repopulating Human Cord Blood Cells," *Gene Transfer: Biology and Marking Studies*, Abstract No. 877, p. 250a, 2003.
Imren et al., "Permanent and panerythroid correction of murine B thalassemia by multiple lentiviral integration in hematopoietic stem cells," *PNAS*, 99(2):14380-14385, 2002.
International Search Report for PCT/US03/039526, dated Oct. 19, 2004.
Iwakuma et al., "Self-Inactivating Lentiviral Vectors with U3 and U5 Modifications," *Virology*, 261:120-132, 1999.
Kaye et al., *Proc. Natl. Acad. Sci. USA*, 87:6922-6926, 1990.
LeBoulch et al., Geneseq Accession No. ABZ69006, computer printout pp. 1-3.
Pawliuk et al. "Correction of Sickle Cell Disease in Transgenic Mouse Models by Hematopoietic Stem Cell Gene Therapy," *Blood*, 98(11), Part 1:781a, 2001.
Pawliuk et al., "Correction of Sickle Cell Disease in Transgenic Mouse Models by Gene Therapy," *Science*, 294:2368-2371, 2001.
Pellinen et al., *International Journal of Oncology*, 25:1753-1762, 2004.
Ramezani et al., "Development of Improved Lentiviral Vectors for Hemophilia A Gene Therapy," *In Vivo Gene Transfer*, Abstract No. 3428, p. 869a, 2002.
Rivella et al., "Therapeutic haemoglobin synthesis in beata-thalassaemic mice expressing lentvirus-encoded human beta-globin," *Nature*, 406(6791):82-86, 2000.
Rudinger, *Peptide Hormones, Parsons, University Park Press*, Baltimore, p. 1-7, 1976.
Skolnick et al., *Trends in Biotech*, 18:34-39, 2000.
Smallwood et al., *Virology*, 304:135-145, 2002.
Thomas, Nature Reviews/Genetics, 4:346-358, 2003.
Tomasinsig et al., *Current Protein and Peptide Science*, 6:23-34, 2005.
Verma et al., *Nature*, vol. 389:239-242, 1997.
Yannaki et al., "Topological Constraints Governing the Use of the Chicken HS4 Chromatin Insulator in Oncoretrovirus Vectors," *Molecular Therapy*, 5(5):589-598, 2002.
Bahçeci, et al., "CD34. cell dose predicts relapse and survival after T-cell-depleted HLA-identical haematopoietic stem cell transplantation (HSCT) for haematological malignancies." British Journal of Haematology (2000); 108(2): 408-414.
Cavazzana, et al., "Longer-Term Follow-up on the First Patients with Severe Hemoglobinopathies Treated with LentiGlobin™ Gene Therapy." ASH 59th Annual Meeting & Exposition (2017), Abstract #4609, Assoc. Society Hematology Annual Meeting Dec. 12, 2017, Atlanta, GA, 1 page.
Podestà, "Transplantation hematopoiesis." Curr Opin Hematol. (2001); 8(6): 331-336.
Weaver, et al., "An analysis of engraftment kinetics as a function of the CD34 content of peripheral blood progenitor cell collections in 692 patients after the administration of myeloablative chemotherapy." Blood (1995); 86: 3961-3969.

* cited by examiner

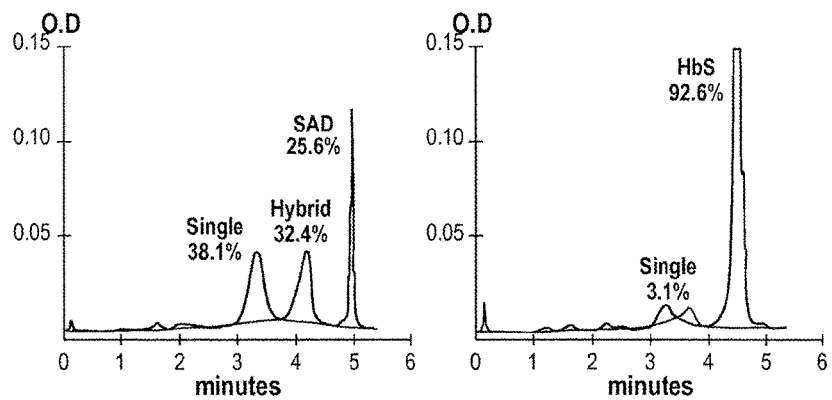
*Fig. 3A*    *Fig. 3B*
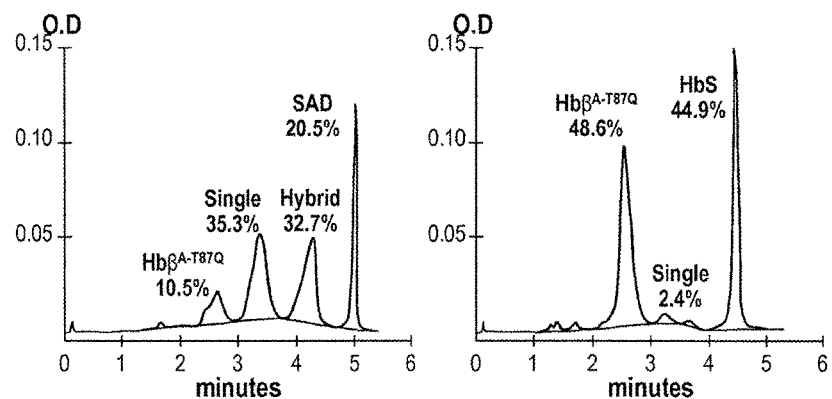
*Fig. 3C*    *Fig. 3D*

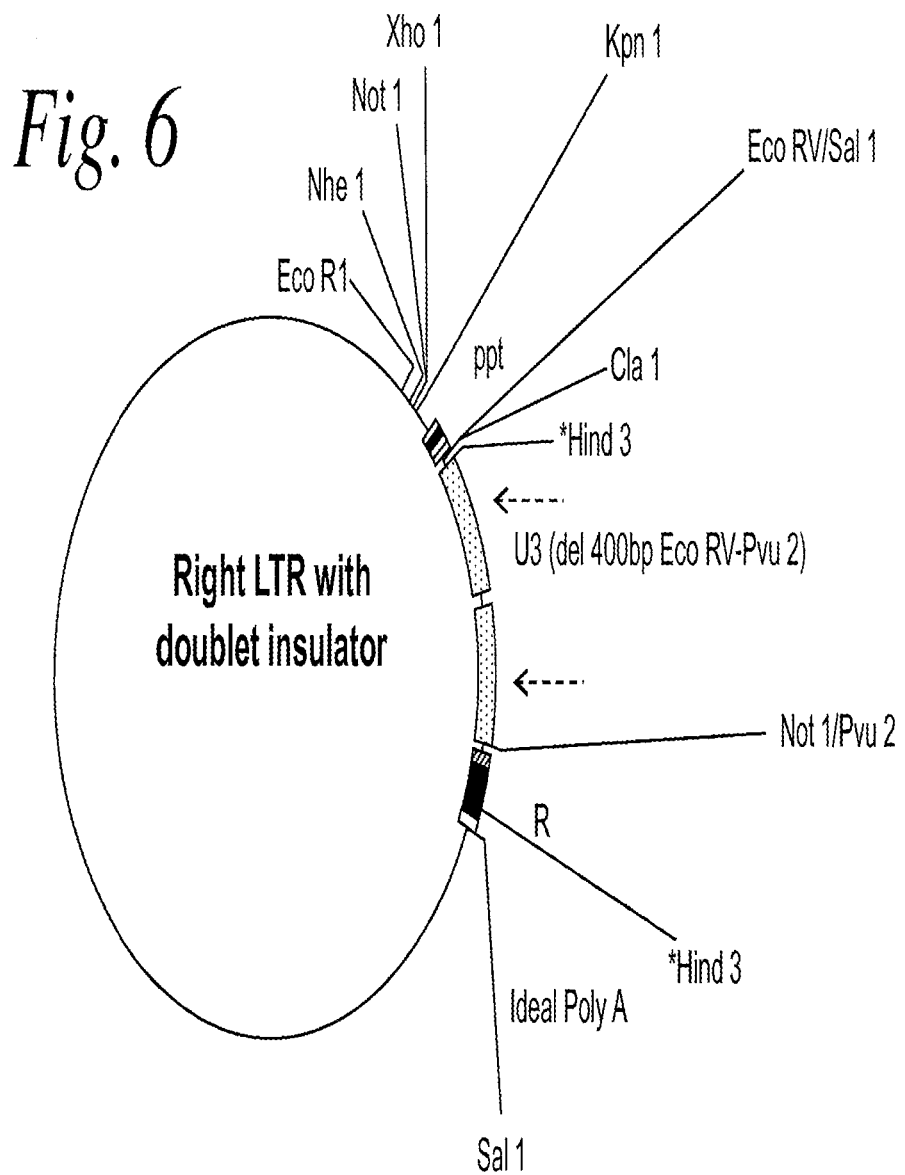

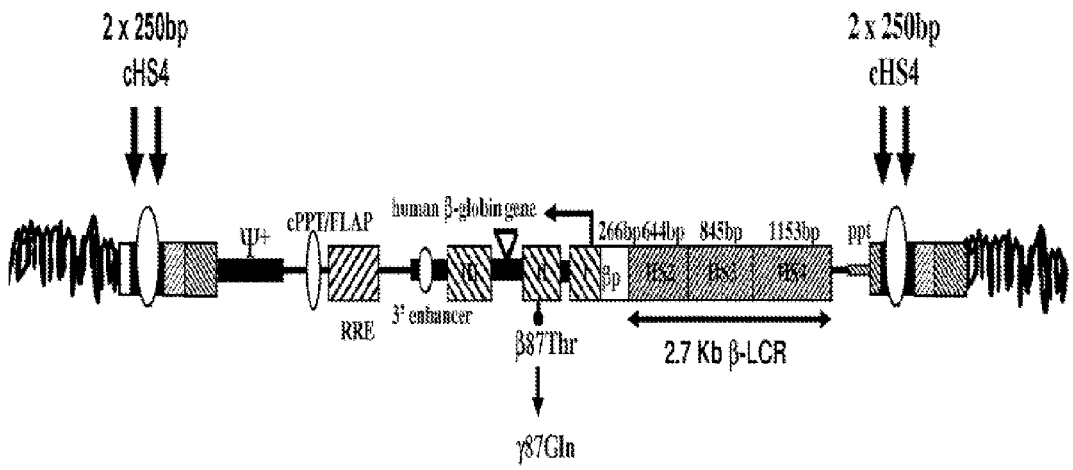
FIG. 13A
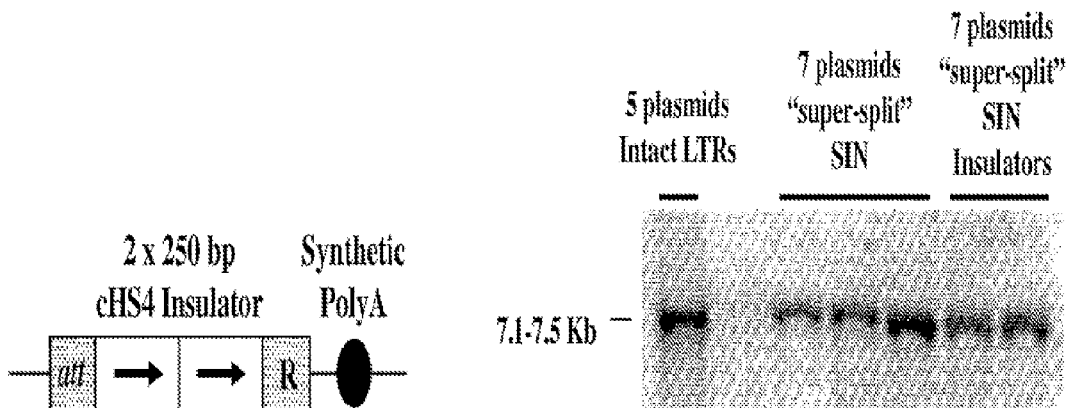
FIG. 13B
FIG. 13C

THERAPEUTIC RETROVIRAL VECTORS FOR GENE THERAPY

CROSS REFERENCE TO RELATED APPLICATIONS

This application is a divisional of U.S. patent application Ser. No. 13/242,815, filed on Sep. 23, 2011, now allowed, which is a continuation of U.S. patent application Ser. No. 12/976,078, filed on Dec. 22, 2010, which is a continuation of U.S. patent application Ser. No. 11/150,785, filed on Jun. 9, 2005 (issued U.S. Pat. No. 7,901,671), which is a continuation of International Patent Application Serial Number PCT/US03/039526, filed on Dec. 11, 2003, which claims priority to U.S. Provisional Application No. 60/433,321, filed on Dec. 13, 2002; U.S. Provisional Application No. 60/475,822, filed on Jun. 4, 2003; and U.S. Provisional Application No. 60/513,312, filed on Oct. 21, 2003. The contents of each of the aforementioned applications are hereby incorporated by reference herein.

STATEMENT REGARDING SEQUENCE LISTING

The Sequence Listing associated with this application is provided in text format in lieu of a paper copy, and is hereby incorporated by reference into the specification. The name of the text file containing the Sequence Listing is BLBD_014_06_US_ST25.txt. The text file is 7 KB, was created on Apr. 29, 2015, and is being submitted electronically via EFS-Web.

BACKGROUND OF THE INVENTION

Hemoglobinopathies encompass a number of anemias of genetic origin in which there is decreased production and/or increased destruction (hemolysis) of red blood cells (RBCs). The blood of normal adult humans contains hemoglobin (designated as HbA) which contains two pairs of polypeptide chains designated alpha and beta. Fetal hemoglobin (HbF), which produces normal RBCs, is present at birth, but the proportion of HbF decreases during the first months of life and the blood of a normal adult contains only about 2% HbF. There are genetic defects which result in the production by the body of abnormal hemoglobins with a concomitant impaired ability to maintain oxygen concentration. Among these genetically derived anemias are included thalassemia, Cooley's Disease and sickle cell disease.

Sickle cell disease (SCD) is one of the most prevalent autosomal recessive diseases worldwide. SCD became the first genetic disorder for which a causative mutation was identified at the molecular level: the substitution of valine for glutamic acid in human $\beta^A$-globin codon 6 (Ingram (1957) *Nature*, 180:326). In homozygotes the abnormal hemoglobin (Hb) [HbS ($\alpha_2\beta^S_2$)] polymerizes in long fibers upon deoxygenation within red blood cells (RBCs), which become deformed or "sickled," rigid, and adhesive, thereby triggering microcirculation occlusion, anemia, infarction, and organ damage (Stamatoyannopoulos, et al. (eds) (1994) *The Molecular Basis of Blood Diseases*, Saunders, Pa., ed. 2; 207-256; Nagel, et al. (2001) *Disorders of Hemoglobin*, Cambridge Univ. Press, Cambridge; 711-756).

Human γ-globin is a strong inhibitor of HbS polymerization, in contrast to human $\beta^A$-globin, which is effective only at very high concentrations (Bookchin et al. (1971) *J. Mol. Biol.* 60:263). Hence, gene therapy of SCD was proposed by means of forced expression of γ-globin or γ/β hybrids in adult RBCs after gene transfer to hematopoietic stem cells (HSCs) (McCune et al. (1994) *PNAS USA* 91:9852; Takekoshi et al. (1995) *PNAS USA* 92:3014; Miller et al. (1994) *PNAS USA* 91:10183; Emery et al. (1999) Hum. *Gene Ther.* 10:877; Rubin et al. (2000) *Blood* 95: 3242; Sabatino et al. (2000) *PNAS USA* 97:13294; Blouin et al. (2000) *Nat. Med.* 6:177).

Although the discovery of the human β-globin locus control region (LCR) held promise to achieve high globin gene expression levels (Tuan et al. (1985) *PNAS USA* 82:6384; Grosveld et al. (1987) *Cell* 51:975), the stable transfer of murine onco-retroviral vectors encompassing minimal core elements of the LCR proved especially challenging (Gelinas et al. (1992) *Bone Marrow Transplant* 9:157; Chang et al. (1992) *PNAS USA* 89:3107; Plavec et al. (1993) *Blood* 81:1384; Leboulch et al. (1994) EMBO J 13:3065; Sadelain et al. (1995) *PNAS USA* 92:6728; Raftopoulos et al. (1997) *Blood* 90:3414; Kalberer et al. (2000) *PNAS USA* 97:5411). To allow the transfer of larger LCR and globin gene sequences, one proposal was the use of RNA splicing and export controlling elements that include the Rev/R responsive element (RRE) components of human immunodeficiency virus (HIV) (Alkan et al. (31 May 2000) paper presented at the 3rd American Society of Gene Therapy, Denver, Colo.), and an RRE-bearing HIV-based lentiviral vector which had resulted in substantial amelioration of β-thalassemia in transplanted mice (May et al. (2000) *Nature* 406:82). This approach was not sufficient for complete correction, however, as gene expression remained heterocellular, and the amount of human $\beta^A$-globin found incorporated in Hb tetramers in a nonthalassemic background was unlikely to be successful therapy for SCD (May et al., supra). Accordingly, there remains a need for a gene therapy approach which can successfully treat SCD and other hemoglobinopathies.

SUMMARY OF THE INVENTION

The present invention provides improved compositions and methods for achieving gene therapy in hematopoietic cells and hematopoietic precursor cells, including erythrocytes, erythroid progenitors, and embryonic stem cells. The invention further provides improved gene therapy methods for treating hematopoietic-related disorders.

In one embodiment, the invention provides an improved gene therapy vector optimized to express high levels of one or more therapeutic proteins in erythroid cells or erythroid precursor cells. In a particular embodiment, the vector comprises an optimized retroviral vector which expresses one or more antisickling proteins at therapeutic levels in order to treat hemoglobinopathies. Retroviral vectors, including lentiviral vectors, employed in the gene delivery system of the present invention are highly efficient at infecting and integrating in a non-toxic manner into the genome of erythroid cells, and maintaining therapeutic levels of erythroid-specific gene expression. In a particular embodiment, the retroviral vector of the invention comprises a left (5') retroviral LTR; a retroviral export element, optionally a lentiviral reverse response element (RRE); a promoter, or active portion thereof, and a locus control region (LCR), or active portion thereof, operably linked to a gene of interest; and a right (3') retroviral LTR. The retroviral vector of the invention can further comprise a central polypurine tract/DNA flap (cPPT/FLAP), including, for example, a cPPT/FLAP from HIV-1. In one embodiment, the retrovirus is a lentivirus, including, for example, HIV. In another embodiment, the promoter of the 5' LTR is replaced with a heterologous promoter, including, for example, cytomegalovirus (CMV) promoter, Retroviral vectors, including lentiviral vectors, of the invention further comprise a gene of interest, including, for example, a globin gene or a gene which encodes an antisickling protein. In one embodiment, the globin gene expressed in the retroviral vector of the invention is β-globin, δ-globin, or γ-globin. In another embodiment, the human β-globin gene is the wild type human β-globin gene or human $β^A$-globin gene. In another embodiment, the human β-globin gene comprises one or more deletions of intron sequences or is a mutated human β-globin gene encoding at least one antisickling amino acid residue. Antisickling amino acids can be derived from human δ-globin or human γ-globin. In another embodiment, the mutated human β-globin gene encodes a threonine to glutamine mutation at codon 87 ($β^{A-T87Q}$).

Retroviral vectors, including lentiviral vectors, of the invention can be used in gene therapy, including for the treatment of hemoglobinopathies. The invention also includes host cells comprising, e.g., transfected with, the vectors of the invention. In one embodiment, the host cell is an embryonic stem cell, a somatic stem cell, or a progenitor cell.

In other embodiments, the invention provides methods for using the foregoing optimized vectors to achieve stable, high levels of gene expression in erythroid cells, e.g., in order to treat erythroid-specific diseases. In a particular embodiment, the gene therapy vectors are used to treat hemoglobinopathies, including, for example, sickle cell disease (SCD). In another embodiment, the gene therapy vectors are used for treatment of thalassemias, including, but not limited to, β-thalassemia.

In yet other embodiments, the invention provides a self-inactivating (SIN) retroviral vector comprising a left (5') retroviral LTRa retroviral export element, optionally a lentiviral reverse response element (RRE); a promoter, or active portion thereof, and a locus control region (LCR), or active portion thereof, operably linked to a gene of interest; and a right (3') retroviral LTR, wherein the U5 region of the left (5') LTR, the right (3') LTR, or both the left and right LTRs are modified to replace all or a portion of the region with an ideal poly(A) sequence and the U3 region of the left (5') long terminal repeat (LTR), the right (3') LTR, or both the left and right LTRs are modified to include one or more insulator elements. In one embodiment the U3 region is modified by deleting a fragment of the U3 region and replacing it with an insulator element. In yet another embodiment, the U5 region of the right (3') LTR is modified by deleting the U5 region and replacing it with a DNA sequence, for example an ideal poly(A) sequence. In yet another embodiment, the vector further comprises a central polypurine tract/DNA flap (cPPT/FLAP). In still another embodiment, the vector comprises an insulator element comprising an insulator from an α-globin locus, including, for example, chicken HS4

In another embodiment of the invention, the vector includes a nucleic acid cassette comprising a suicide gene operably linked to a promoter. In a particular embodiment, the suicide gene is HSV thymidine kinase (HSV-Tk). The vector can also include a nucleic acid cassette comprising a gene for in vivo selection of the cell, such as a gene for in vivo selection, e.g., a methylguanine methyltransferase (MGMT) gene.

BRIEF DESCRIPTION OF THE FIGURES

FIG. 2a shows circulating RBCs from recipient mice were fixed permeabilized, stained with a FITC-labeled antibody that specifically recognizes human β-globin (Perkin-Elmer Wallac, Norton Ohio), and subsequently analyzed by FACS. Top: representative mouse transplanted with mock-transduced bone marrow cells. Bottom: representative mouse transplanted with bone marrow transduced with the $β^{A-T87Q}$-globin lentivirus. FIG. 2b shows results from primer extension analysis of peripheral blood RNA. Lanes 1, 3, 5, 7, and 9: amplification with primers specific for the endogenous murine β-single globin mRNA generating a 53-base pair (bp) DNA fragment. Lanes 2, 4, 6, 8, and 10: amplification with primers specific for the human $β^{A-T87Q}$-globin mRNA generating a 90-bp DNA fragment. Lanes 1 and 2: mock-transduced mouse. Lanes 3 and 4: transgenic control mouse expressing 86% of human β-globin mRNA. Lanes 5 to 10: three C57BL/6 recipients of $β^{A-T87Q}$-globin-transduced bone marrow cells (lanes 5 and 6, mouse #1; 7 and 8 mouse #2; 9 and 10, mouse #3). FIG. 2c graphically depicts HPLC profiles of globin chains extracted from RBCs of a mock-transduced mouse (top) and a recipient of human $β^{A-T87Q}$-globin-transduced bone marrow (bottom).

FIGS. 3a-3d graphically depict HPLC profiles of Hb extracted from RBCs of mouse recipients of mock-transduced SAD (FIG. 3a), mock-transduced BERK (FIG. 3b), $β^{A-T87Q}$-globin-transduced SAD (FIG. 3c), and $β^{A-T87Q}$-globin-transduced BERK bone marrow cells (FIG. 3d).

FIG. 5a shows Nomarski optics microscopy of RBCs from mice transplanted with either (top) mock- or (bottom) $β^{A-T87Q}$- globin lentivirus-transduced BERK bone marrow cells under 5% pO$_2$ 3 months after transplantation. FIG. 5b shows quantification of the percentage of sickle RBCs from recipients of mock-transduced and $\beta^{A-T87Q}$-globin-transduced BERK or SAD bone marrow under 5% or 13% oxygen conditions, respectively. Error bars indicate SE; *, P=0.01; †-, P=0.03. FIG. 5c shows the relationship between log of reciprocal delay time (dt) of HbS polymerization and Hb concentration of RBC lysates. Time courses of Hb polymerization in lysates were performed at various concentrations by the temperature jump method. Δ, lysate from homozygote SS patient; ▲, lysate from an asymptomatic AS sickle cell trait patient; □, lysate from a mouse recipient of mock-transduced SAD marrow; ■, lysate from a mouse recipient of $\beta^{A-T87Q}$-globin-transduced SAD marrow; ○, lysate from mouse recipient of mock-transduced BERK marrow; ●, lysate from a mouse recipient of $\beta^{A-T87Q}$-globin-transduced BERK marrow. FIG. 5d shows Percoll-Larex continuous density gradients from blood of recipient mice. Lane 1, density marker beads; lanes 2 and 6, C57BL/6 controls; lanes 3 and 7, SAD and BERK controls, respectively; lanes 4 and 5, C57BL/6 recipients of mock-transduced or $\beta^{A-T87Q}$-transduced SAD bone marrow, respectively; lane 8, C57BL/6 recipient of $\beta^{0A-T87Q}$-transduced BERK bone marrow; lane 9, transgenic BERK mouse expressing human γ-globin at ~100% of $\beta^S$-globin. FIG. 5e shows spleens from nontransplanted (1) BERK and (2) C57BL/6 mice or C57BL/6 mice transplanted with either (3) $\beta^{A-T87Q}$-transduced or (4) mock-transduced BERK bone marrow.

FIG. 6 graphically depicts a map of a vector comprising a right LTR with a doublet insulator.

FIGS. 13a-13c graphically depict the SIN vector and titer analysis for the SIN vector. FIG. 13a graphically depicts the organization of the SIN vector, including the modifications to the LTR. FIG. 13b shows a detailed schematic of the modification, wherein the U3 region of the LTR is replaced with a cHS4 insulator and the U5 region is replaced with an ideal polyA sequence. FIG. 13c shows a Southern blot which examines the titer for the insulator SIN vector containing β-globin.

FIG. 14a graphically depicts the the human β-globin ($\beta^A$) lentiviral vector. FIG. 14b shows the proportion of peripheral blood RBCs expressing human β-globin, as assessed by FACS after staining the cells with an antibody specific for human β-globin. FIG. 14c shows expression of human β globin in red blood cells (RBCs) of reconstituted mice. The upper left of FIG. 14c shows FACS analysis of RBCs from a representative recipient of lenti-GFP-virus-transduced THAL bone marrow cells, where RBCs from an unmanipulated mouse were used as a negative control. The upper right and lower left of FIG. 14c show results from FACS analysis of RBCs from a representative recipient of lenti-β globin-virus-transduced THAL bone marrow cells at 2 and 7 months after transplantation. The lower right of FIG. 14c shows results from FACS analysis of RBCs from one of the secondary recipients transplanted with bone marrow cells from a primary donor at 6 months after transplantation.

DETAILED DESCRIPTION OF THE INVENTION

Figure 1A:
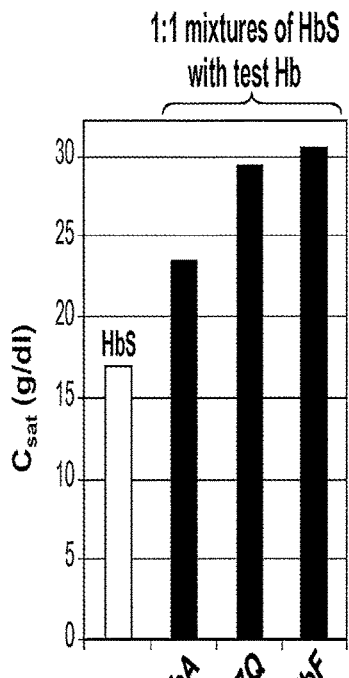
FIG. 1a graphically shows that $β^{A-T87Q}$ and HbF are potent inhibitors of HbS polymerization in vitro in contrast to HbA.

The present invention provides improved compositions and methods for gene therapy, particularly in the treatment of hemoglobinopathies. In one embodiment, improved lentiviral vectors are use to deliver therapeutic gene products to embryonic stem cells, somatic stem cells, or hematopoietic stem cells, including, but not limited to, erythroid progenitors. In another embodiment, improved lentiviral vectors are used to deliver therapeutic genes to erythrocytes, thereby providing sustained, high level expression of therapeutic proteins specifically in erythroid cells. In a particular embodiment, the expression is permanent (e.g., panerythroid).

I. Definitions

As used herein, the following terms and phrases used to describe the invention shall have the meanings provided below.

The term "retrovirus" refers to any known retrovirus (e.g., type c retroviruses, such as Moloney murine sarcoma virus (MoMSV), Harvey murine sarcoma virus (HaMuSV), murine mammary tumor virus (MuMTV), gibbon ape leukemia virus (GaLV), feline leukemia virus (FLV), Spumavirus, Friend, Murine Stem Cell Virus (MSCV) and Rous Sarcoma Virus (RSV)). "Retroviruses" of the invention also include human T cell leukemia viruses, HTLV-1 and HTLV-2, and the lentiviral family of retroviruses, such as Human Immunodeficiency Viruses, HIV-1, HIV-2, simian immnodeficiency virus (SIV), feline immunodeficiency virus (FIV), equine immnodeficiency virus (EIV), and other classes of retroviruses.

Retroviruses are RNA viruses that utilize reverse transcriptase during their replication cycle. The retroviral genomic RNA is converted into double-stranded DNA by reverse transcriptase. This double-stranded DNA form of the virus is capable of being integrated into the chromosome of the infected cell; once integrated, it is referred to as a "provirus." The provirus serves as a template for RNA polymerise II and directs the expression of RNA molecules which encode the structural proteins and enzymes needed to produce new viral particles.

At each end of the provirus are structures called "long terminal repeats" or "LTRs." The term "long terminal repeat (LTR)" refers to domains of base pairs located at the ends of retroviral DNAs which, in their natural sequence context, are direct repeats and contain U3, R and U5 regions. LTRs generally provide functions fundamental to the expression of retroviral genes (e.g., promotion, initiation and polyadenylation of gene transcripts) and to viral replication. The LTR contains numerous regulatory signals including transcriptional control elements, polyadenylation signals and sequences needed for replication and integration of the viral genome. The viral LTR is divided into three regions called U3, R and U5. The U3 region contains the enhancer and promoter elements. The U5 region is the sequence between the primer binding site and the R region and contains the polyadenylation sequence. The R (repeat) region is flanked by the U3 and U5 regions. The LTR composed of U3, R and U5 regions, appears at both the both the 5' and 3' ends of the viral genome. In one embodiment of the invention, the promoter within the LTR, including the 5' LTR, is replaced with a heterologous promoter. Examples of heterologous promoters which can be used include, for example, the cytomegalovirus (CMV) promoter.

The term "lentivirus" refers to a group (or genus) of retroviruses that give rise to slowly developing disease. Viruses included within this group include HIV (human immunodeficiency virus; including HIV type 1, and HIV type 2), the etiologic agent of the human acquired immunodeficiency syndrome (AIDS); visna-maedi, which causes encephalitis (visna) or pneumonia (maedi) in sheep, the caprine arthritis-encephalitis virus, which causes immune deficiency, arthritis, and encephalopathy in goats; equine infectious anemia virus, which causes autoimmune hemolytic anemia, and encephalopathy in horses; feline immunodeficiency virus (FIV), which causes immune deficiency in cats; bovine immune deficiency virus (BIV), which causes lymphadenopathy, lymphocytosis, and possibly central nervous system infection in cattle; and simian immunodeficiency virus (SIV), which cause immune deficiency and encephalopathy in sub-human primates. Diseases caused by these viruses are characterized by a long incubation period and protracted course. Usually, the viruses latently infect monocytes and macrophages, from which they spread to other cells. HIV, FIV, and SIV also readily infect T lymphocytes (i.e., T-cells).

The term "hybrid" refers to a vector, LTR or other nucleic acid containing both lentiviral sequences and non-lentiviral retroviral sequences.

The term "vector" refers to a nucleic acid molecule capable of transporting another nucleic acid to which it has been linked. The term "expression vector" includes any vector, (e.g., a plasmid, cosmid or phage chromosome) containing a gene construct in a form suitable for expression by a cell (e.g., linked to a promoter). In the present specification, "plasmid" and "vector" are used interchangeably, as a plasmid is a commonly used form of vector. Moreover, the invention is intended to include other vectors which serve equivalent functions.

The term "retroviral vector" refers to a vector containing structural and functional genetic elements that are primarily derived from a retrovirus.

The term "lentiviral vector" refers to a vector containing structural and functional genetic elements outside the LTRs that are primarily derived from a lentivirus.

The term "self-inactivating vector" refers to vectors in which the right (3') LTR enhancer-promoter region, know as the U3 region, has been modified (e.g., by deletion or substitution) to prevent viral transcription beyond the first round of viral replication. Consequently, the vectors are capable of infecting and then integrating into the host genome only once, and can not be passed further. This is because the right (3') LTR U3 region is used as a template for the left (5') LTR U3 region during viral replication and, thus, the viral transcript can not be made without the U3 enhancer-promoter. If the viral transcript is not made, it can not be processed or packaged into virions, hence the life cycle of the virus ends. Accordingly, SIN vectors greatly reduce risk of creating unwanted replication-competent virus since the right (3') LTR U3 region has been modified to prevent viral transcription beyond the first round of replication, hence eliminating the ability of the virus to be passed.

The term "TAR" refers to the "trans-activation response" genetic element located in the R region of lentiviral (e.g., HIV) LTRs. This element interacts with the lentiviral transactivator (tat) genetic element to enhance viral replication.

The term "R region" refers to the region within retroviral LTRs beginning at the start of the capping group (i.e., the start of transcription) and ending immediately prior to the start of the poly A tract. The R region is also defined as being flanked by the U3 and U5 regions. The R region plays an important role during reverse transcription in permitting the transfer of nascent DNA from one end of the genome to the other.

The term "transfection" refers to the introduction of foreign DNA into eukaryotic cells. Transfection may be accomplished by a variety of means known in the art including but not limited to calcium phosphate-DNA co-precipitation, DEAE-dextran-mediated transfection, polybrene-mediated transfection, electroporation, microinjection, liposome fusion, lipofection, protoplast fusion, retroviral infection, and biolistics.

The term "transduction" refers to the delivery of a gene(s) using a viral or retroviral vector by means of viral infection rather than by transfection. In preferred embodiments, retroviral vectors are transduced by packaging the vectors into virions prior to contact with a cell. For example, an anti-HIV gene carried by a retroviral vector can be transduced into a cell through infection and provirus integration.

The term "promoter/enhancer" refers to a segment of DNA which contains sequences capable of providing both promoter and enhancer functions. For example, the long terminal repeats of retroviruses contain both promoter and enhancer functions. The enhancer/promoter may be "endogenous" or "exogenous" or "heterologous." An "endogenous" enhancer/promoter is one which is naturally linked with a given gene in the genome. An "exogenous" or "heterologous" enhancer/promoter is one which is placed in juxtaposition to a gene by means of genetic manipulation (i.e., molecular biological techniques) such that transcription of that gene is directed by the linked enhancer/promoter.

Efficient expression of recombinant DNA sequences in eukaryotic cells requires expression of signals directing the efficient termination and polyadenylation of the resulting transcript. Transcription termination signals are generally found downstream of the polyadenylation signal. The term "poly A site" or "poly A sequence" as used herein denotes a DNA sequence which directs both the termination and polyadenylation of the nascent RNA transcript. Efficient polyadenylation of the recombinant transcript is desirable as transcripts lacking a poly A tail are unstable and are rapidly degraded. The poly A signal utilized in an expression vector may be "heterologous" or "endogenous." An endogenous poly A signal is one that is found naturally at the 3' end of the coding region of a given gene in the genome. A heterologous poly A signal is one which is one which is isolated from one gene and placed 3' of another gene.

The term "export element" refers to a cis-acting post-transcriptional regulatory element which regulates the transport of an RNA transcript from the nucleus to the cytoplasm of a cell. Examples of RNA export elements include, but are not limited to, the human immunodeficiency virus (HIV) rev response element (RRE) (see e.g., Cullen et al. (1991) *J. Virol.* 65: 1053; and Cullen et al. (1991) Cell 58: 423), and the hepatitis B virus post-transriptional regulatory element (PRE) (see e.g., Huang et al. (1995) *Molec. and Cell. Biol.* 15(7): 3864; Huang et al. (1994) J. Virol. 68(5): 3193; Huang et al. (1993) *Molec. and Cell. Biol.* 13(12): 7476), and U.S. Pat. No. 5,744,326). Generally, the RNA export element is placed within the 3' UTR of a gene, and can be inserted as one or multiple copies. RNA export elements can be inserted into any or all of the separate vectors generating the packaging cell lines of the present invention.

The phrase "retroviral packaging cell line" refers to a cell line (typically a mammalian cell line) which contains the necessary coding sequences to produce viral particles which lack the ability to package RNA and produce replication-competent helper-virus. When the packaging function is provided within the cell line (e.g., in trans by way of a plasmid vector), the packaging cell line produces recombinant retrovirus, thereby becoming a "retroviral producer cell line."

The term "nucleic acid cassette" as used herein refers to genetic sequences within the vector which can express a RNA, and subsequently a protein. The nucleic acid cassette contains the gene of interest. The nucleic acid cassette is positionally and sequentially oriented within the vector such that the nucleic acid in the cassette can be transcribed into RNA, and when necessary, translated into a protein or a polypeptide, undergo appropriate post-translational modifications required for activity in the transformed cell, and be translocated to the appropriate compartment for biological activity by targeting to appropriate intracellular compartments or secretion into extracellular compartments. Preferably, the cassette has its 3' and 5' ends adapted for ready insertion into a vector, e.g., it has restriction endonuclease sites at each end. In a preferred embodiment of the invention, the nucleic acid cassette contains the sequence of a therapeutic gene used to treat a hemoglobinopathic condition. The cassette can be removed and inserted into a vector or plasmid as a single unit.

As used herein, the term "gene of interest" refers to the gene inserted into the polylinker of an expression vector. In one embodiment, the gene of interest encodes a gene which provides a therapeutic function for the treatment of a hemoglobinopathy.

The term "promoter" as used herein refers to a recognition site of a DNA strand to which the RNA polymerase binds. The promoter forms an initiation complex with RNA polymerase to initiate and drive transcriptional activity. The complex can be modified by activating sequences termed "enhancers" or inhibitory sequences termed "silencers".

As used herein, the term "cis" is used in reference to the presence of genes on the same chromosome. The term "cis-acting" is used in reference to the controlling effect of a regulatory gene on a gene present on the same chromosome. For example, promoters, which affect the synthesis of downstream mRNA are cis-acting control elements.

The term "suicide gene" is used herein to define any gene that expresses a product that is fatal to the cell expressing the suicide gene. In one embodiment, the suicide gene is cis-acting in relation to the gene of interest on the vector of the invention, Examples of suicide genes are known in the art, including HSV thymidine kinase (HSV-Tk).

The term "operably linked", refers to a juxtaposition wherein the components described are in a relationship permitting them to function in their intended manner. In one embodiment, the term refers to a functional linkage between a nucleic acid expression control sequence (such as a promoter, or array of transcription factor binding sites) and a second nucleic acid sequence, wherein the expression control sequence directs transcription of the nucleic acid corresponding to the second sequence.

The terms "transformation," "transfection," and "transduction" refer to introduction of a nucleic acid, e.g., a viral vector, into a recipient cell.

The terms "pseudotype" or "pseudotyping" as used herein, refer to a virus whose viral envelope proteins have been substituted with those of another virus possessing preferable characteristics. For example, HIV can be pseudotyped with vesicular stomatitis virus G-protein (VSV-G) envelope proteins, which allows HIV to infect a wider range of cells because HIV envelope proteins (encoded by the env gene) normally target the virus to CD4+ presenting cells. In a preferred embodiment of the invention, lentiviral envelope proteins are pseudotyped with VSV-G.

As used herein, the term "packaging" refers to the process of sequestering (or packaging) a viral genome inside a protein capsid, whereby a virion particle is formed. This process is also known as encapsidation. As used herein, the term "packaging signal" or "packaging sequence" refers to sequences located within the retroviral genome which are required for insertion of the viral RNA into the viral capsid or particle. Several retroviral vectors use the minimal packaging signal (also referred to as the psi [ψ] sequence) needed for encapsidation of the viral genome. Thus, as used herein, the terms "packaging sequence," "packaging signal," "psi" and the symbol "ψ," are used in reference to the non-coding sequence required for encapsidation of retroviral RNA strands during viral particle formation.

As used herein, the term "packaging cell lines" is used in reference to cell lines that do not contain a packaging signal, but do stably or transiently express viral structural proteins and replication enzymes (e.g., gag, pol and env) which are necessary for the correct packaging of viral particles.

As used herein, the term "replication-defective" refers to virus that is not capable of complete, effective replication such that infective virions are not produced (e.g. replication-defective lentiviral progeny). The term "replication-competent" refers to wild-type virus or mutant virus that is capable of replication, such that viral replication of the virus is capable of producing infective virions (e.g., replication-competent lentiviral progeny).

As used herein, the term "incorporate" refers to uptake or transfer of a vector (e.g., DNA or RNA) into a cell such that the vector can express a therapeutic gene product within the cell. Incorporation may involve, but does not require, integration of the DNA expression vector or episomal replication of the DNA expression vector.

As used herein, the term "erythroid-specific expression" or "red blood cell-specific expression" refers to gene expression which only occurs in erythrocytes or red blood cells (RBCs), used interchangeably herein.

The term "gene delivery" or "gene transfer" refers to methods or systems for reliably inserting foreign DNA into target cells, such as into muscle cells. Such methods can result in transient or long term expression of genes. Gene transfer provides a unique approach for the treatment of acquired and inherited diseases. A number of systems have been developed for gene transfer into mammalian cells. See, e.g., U.S. Pat. No. 5,399,346. The lentiviral vector of the invention is optimized to express antisickling proteins at therapeutic levels in virtually all circulating RBCs.

The term "stem cell" refers to the cell from which a progenitor cell is derived. Stem cells are defined by their ability to self-renew. Stem cells include, for example, embryonic stem cells and somatic stem cells. Hematopoietic stem cells can generate daughter cells of any of the hematopoietic lineages. Stem cells with long term hematopoietic reconstituting ability can be distinguished by a number of physical and biological properties from differentiated cells and progenitor cells (see, e.g., Hodgson, G. S. & Bradley, T. R., Nature, Vol. 281, pp 381-382; Visser et al., J. Exp. Med., Vol. 59, pp. 1576-1590, 1984; Spangrude et al., Science, Vol. 241, pp. 58-62, 1988; Szilvassy et al., Blood, Vol. 74, pp. 930-939, 1989; Ploemacher, R. E. & Brons, R. H. C., Exp. Hematol., Vol. 17, pp. 263-266, 1989).

The term "embryonic stem cell" is used herein to mean an undifferentiated, pluripotent cell derived from a blastula stage embryo.

The term "somatic stem cell" is used here to mean cells in the body which have the unique ability to regenerate themselves and differentiate into many different types of cells. Examples of somatic stem cells include blood stem cells, muscle/bone stem cells, brain stem cells, and liver stem cells.

As used herein, the term "progenitor" or "progenitor cells" refers to cells which are the precursors of differentiating cells. Many progenitor cells differentiate along a single lineage, but may have quite extensive proliferative capacity. Examples of progenitor cells include, but are not limited to, pluripotent stem cells, totipotent stem cells, myeloid stem cells, and lymphoid stem cells.

The term "globin" is used here to mean all proteins or protein subunits that are capable of covalently or noncovalently binding a heme moiety, and can therefore transport or store oxygen. Subunits of vertebrate and invertebrate hemoglobins, vertebrate and invertebrate myoglobins or mutants thereof are included by the term globin. Examples of globins include α-globin or variant thereof, β-globin or variant thereof, a γ-globin or a variant thereof, and δ-globin.

As used herein, "hematopoiesis," refers to the formation and development of blood cells from progenitor cells as well as formation of progenitor cells from stem cells. Blood cells include but are not limited to erythrocytes or red blood cells (RBCs), reticulocytes, monocytes, neutrophils, megakaryotes, eosinophils, basophils, B-cells, macrophages, granulocytes, mast cells, thrombocytes, and leukocytes.

As used herein, the term "hemoglobinopathy" or "hemoglobinopathic condition" includes any disorder involving the presence of an abnormal hemoglobin molecule in the blood. Examples of hemoglobinopathies included, but are not limited to, hemoglobin C disease, hemoglobin sickle cell disease (SCD), sickle cell anemia, and thalassemias. Also included are hemoglobinopathies in which a combination of abnormal hemoglobins are present in the blood (e.g., sickle cell/Hb-C disease).

The term "sickle cell anemia" or "sickle cell disease" is defined herein to include any symptomatic anemic condition which results from sickling of red blood cells. Manifestations of sickle cell disease include: anemia; pain; and/or organ dysfunction, such as renal failure, retinopathy, acute-chest syndrome, ischemia, priapism and stroke. As used herein the term "sickle cell disease" refers to a variety of clinical problems attendant upon sickle cell anemia, especially in those subjects who are homozygotes for the sickle cell substitution in HbS. Among the constitutional manifestations referred to herein by use of the term of sickle cell disease are delay of growth and development, an increased tendency to develop serious infections, particularly due to pneumococcus, marked impairment of splenic function, preventing effective clearance of circulating bacteria, with recurrent infarcts and eventual destruction of splenic tissue. Also included in the term "sickle cell disease" are acute episodes of musculoskeletal pain, which affect primarily the lumbar spine, abdomen, and femoral shaft, and which are similar in mechanism and in severity to the bends. In adults, such attacks commonly manifest as mild or moderate bouts of short duration every few weeks or months interspersed with agonizing attacks lasting 5 to 7 days that strike on average about once a year. Among events known to trigger such crises are acidosis, hypoxia and dehydration, all of which potentiate intracellular polymerization of HbS (J. H. Jandl, Blood: Textbook of Hematology, 2nd Ed., Little, Brown and Company, Boston, 1996, pages 544-545). As used herein, the term "thalassemia" encompasses hereditary anemias that occur due to mutations affecting the synthesis of hemoglobin. Thus, the term includes any symptomatic anemia resulting from thalassemic conditions such as severe or β-thalassemia, thalassemia major, thalassemia intermedia, α-thalassemias such as hemoglobin H disease.

As used herein, "thalassemia" refers to a hereditary disorder characterized by defective production of hemoglobin. Examples of thalassemias include β and α thalassemia. β thalassemias are caused by a mutation in the beta globin chain, and can occur in a major or minor form. In the major form of β thalassemia, children are normal at birth, but develop anemia during the first year of life. The mild form of β thalassemia produces small red blood cells. α thalassemias are caused by deletion of a gene or genes from the globin chain.

As used herein, "antisickling proteins" include proteins which prevent or reverse the pathological events leading to sickling of erythrocytes in sickle cell conditions. In one embodiment of the invention, the lentiviral vector of the invention is used to deliver antisickling proteins to a subject with a hemoglobinopathic condition. Antisickling proteins also include mutated β-globin genes comprising antisickling amino acid residues.

As used herein, the term "self-inactivating" or "SIN," used interchangeably herein, refers to a vector which is modified, wherein the modification greatly reduces the ability of the vector to mobilize once it has integrated into the genome of the recipient, thereby increasing the safety of the use of the vector as a gene delivery vector.

As used herein, the term "insulator" or "insulator element," used interchangeably herein, refers to an exogenous DNA sequence that can be added to a vector of the invention to prevent, upon integration of the vector into a host genome, nearby genomic sequences from influencing expression of the integrated trans-gene(s). Conversely, the insulator element prevents the integrated vector from influencing expression of nearby genomic sequences. This is generally achieved as the insulator is duplicated upon integration of the vector into the genome, such that the insulator flanks the integrated vector (e.g., within the LTR region) and acts to "insulate" the integrated DNA sequence. Suitable insulators for use in the invention include, but are not limited to, the chicken β-Globin insulator (see Chung et al. Cell (1993) 74:505; Chung et al., PNAS (1997) 94:575; and Bell et al. Cell 1999 98:387, incorporated by reference herein). Examples of insulator elements include, but are not limited to, an insulator from an α-globin locus, such as chicken HS4.

II. Retroviral and Lentiviral Vectors

The present invention provides improved methods and compositions for treating hemoglobinopathic conditions using retrovirus-based, e.g., lentivirus-based, gene delivery vectors that which achieve sustained, high-level expression of transferred therapeutic genes in eythroid cells or erythroid precursor cells. In one embodiment of the invention, the vector comprises a self inactivating SIN vector. Particular lentiviral vectors of the invention are described by Pawliuk et al. (2001) Science 294:2368 and Imren et al. (2002) PNAS 99:14380, incorporated by reference herein.

Retroviral and lentiviral vectors of the invention include, but are not limited to, human immunodeficiency virus (e.g., HIV-1, HIV-2), feline immunodeficiency virus (FIV), simian immunodeficiency virus (SIV), bovine immunodeficiency virus (BIV), and equine infectious anemia virus (EIAV). These vectors can be constructed and engineered using art-recognized techniques to increase their safety for use in therapy and to include suitable expression elements and therapeutic genes, such as those described below, which encode therapeutic proteins for treating conditions including, but not limited to, hemoglobinopathies. In one embodiment of the invention, the lentiviral vector is based on HIV-1.

In consideration of the potential toxicity of lentiviruses, the vectors can be designed in different ways to increase their safety in gene therapy applications. For example, the vector can be made safer by separating the necessary lentiviral genes (e.g., gag and pol) onto separate vectors as described, for example, in U.S. patent application Ser. No. 09/311,684, the contents of which are incorporated by reference herein. Thus, recombinant retrovirus can be constructed in which part of the retroviral coding sequence (gag, pol, env) is replaced by a gene of interest rendering the retrovirus replication defective. The replication defective retrovirus is then packaged into virions through the use of a helper virus or a packaging cell line, by standard techniques. Protocols for producing recombinant retroviruses and for infecting cells in vitro or in vivo with such viruses can be found in Current Protocols in Molecular Biology, Ausubel, F. M. et al. (eds.) Greene Publishing Associates, (1989), Sections 9.10-9.14 and other standard laboratory manuals.

A major prerequisite for the use of viruses as gene delivery vectors is to ensure the safety of their use, particularly with regard to the possibility of the spread of wild-type virus in the cell population. The development packaging cell lines, which produce only replication-defective retroviruses, has increased the utility of retroviruses for gene therapy, and defective retroviruses are well characterized for use in gene transfer for gene therapy purposes (for a review see Miller, A. D. (1990) Blood 76:271). Accordingly, in one embodiment of the invention, packaging cell lines are used to propagate vectors (e.g., lentiviral vectors) of the invention to increase the titer of the vector virus. The use of packaging cell lines is also considered a safe way to propagate the virus, as use of the system reduces the likelihood that recombination will occur to generate wild-type virus. In addition, to reduce toxicity to cells that caused by expression of packaging proteins, packaging systems can be use in which the plasmids encoding the packaging functions of the virus are only transiently transfected by, for example, chemical means.

In another embodiment, the vector can be made safer by replacing certain lentiviral sequences with non-lentiviral sequences. Thus, lentiviral vectors of the present invention may contain partial (e.g., split) gene lentiviral sequences and/or non-lentiviral sequences (e.g., sequences from other retroviruses) as long as its function (e.g., viral titer, infectivity, integration and ability to confer high levels and duration of therapeutic gene expression) are not substantially reduced. Elements which may be cloned into the viral vector include, but are not limited to, promoter, packaging signal, LTR(s), polypurine tracts, RRE, etc.

In one embodiment, the retroviral vector of the invention comprises a left (5') retroviral LTR; a retroviral export element, optionally a lentiviral reverse response element (RRE); a promoter, or active portion thereof, and a locus control region (LCR), or active portion thereof, operably linked to a gene of interest; and a right (3') retroviral LTR. Retroviral vectors, including lentiviral vectors, of the invention can further contain a central polypurine tract (cPPT) or DNA flap. The cPPT/DNA flap is used to increase viral titers and transduction efficiency. In a particular embodiment, the cPPT/DNA flap is from HIV-1. In another embodiment, the cPPT/DNA flap increases the efficiency of transfection in to HSCs.

In another embodiment of the invention, the LTR region is modified by replacing the viral LTR promoter with a heterologous promoter. In one embodiment, the promoter of the 5' LTR is replaced with a heterologous promoter. Examples of heterologous promoters which can be used include, but are not limited to, the cytomegalovirus (CMV) promoter which is effective for high level expression.

Retroviral vectors of the invention also include vectors which have been modified to improve upon safety in the use of the vectors as gene delivery agents in gene therapy. In one embodiment of the invention, an LTR region, such as the 3' LTR, of the vector is modified in the U3 and/or U5 regions, wherein a SIN vector is created. Such modifications contribute to an increase in the safety of the vector for gene delivery purposes. In one embodiment, the SIN vector of the invention comprises a deletion in the 3' LTR wherein a portion of the U3 region is replaced with an insulator element. The insulator prevents the enhancer/promoter sequences within the vector from influencing the expression of genes in the nearby genome, and vice/versa, to prevent the nearby genomic sequences from influencing the expression of the genes within the vector. In a further embodiment of the invention, the 3' LTR is modified such that the U5 region is replaced, for example, with an ideal poly(A) sequence. It should be noted that modifications to the LTRs such as modifications to the 3' LTR, the 5' LTR, or both 3' and 5' LTRs, are also included in the invention.

Retroviral vectors of the invention can also comprise elements which control selection of the transduced cell. In one embodiment, the retroviral vector comprises a nucleic acid cassette which allows for in vivo selection of the transduced cell. For example, the nucleic acid cassette could contain the cDNAs for methylguanine methyltransferase (MGMT) or the human glutathione-S-transferase pi (GST pi) which have both been successfully used as in vivo selection markers for transduced hematopoietic stem cells. These transgenes provide chemoprotection to to the combination of 06-benzylguanine (BG) and 1,3-bis (2-chloroethyl)-1-nitrosourea (BCNU) or to transduced cells against posttransplant treatment with cyclophosphamide, respectively. In another embodiment of the invention, the retroviral vector contains a suicide gene operably linked to a promoter. Examples of suicide genes include, but are not limited to, herpes simplex virus (HSV) thymidine kinase (HSV-Tk).

The infectivity of retroviruses, including lentiviruses, is dependent upon the interaction between glycoproteins displayed on the surface of the viral particle and receptors found on the surface of the target cell. HIV is only able to infect T-cells that display the CD4+ receptor on their cell surfaces. To maximize the infectivity of an HIV-based gene delivery system, the lentivirus can be pseudotyped to display a glycoprotein known to bind a wider range of cell type than HIV. In one embodiment of the invention, the recombinant lentivirus is pseudotyped with the vesicular stomatitis virus G coat protein (VSV-G). Pseudotyping with VSV-G increases both the host range and the physical stability of the viral particles, and allows their concentration to very high titers by ultracentrifugation (Naldini et al. (1 996), supra; Aiken (1997) J. *Virol.* 71:5871-5877; Akkina et al., supra; Reiser et al. (1996) *Proc. Natl. Acad. Sci. USA* 93:15266-15271). In a preferred embodiment, the lentiviral vector of the invention is transduced into hematopoietic stem cells (HSCs) after pseudotyping with VSV-G and concentration.

The promoter of the lentiviral vector can be one which is naturally (i.e., as it occurs with a cell in vivo) or non-naturally associated with the 5' flanking region of a particular gene. Promoters can be derived from eukaryotic genomes, viral genomes, or synthetic sequences. Promoters can be selected to be non-specific (active in all tissues), tissue specific, regulated by natural regulatory processes, regulated by exogenously applied drugs, or regulated by specific physiological states such as those promoters which are activated during an acute phase response or those which are activated only in replicating cells. Non-limiting examples of promoters in the present invention include the retroviral LTR promoter, cytomegalovirus immediate early promoter, SV40 promoter, dihydrofolate reductase promoter, and cytomegalovirus (CMV). The promoter can also be selected from those shown to specifically express in the select cell types which may be found associated with conditions including, but not limited to, hemoglobinopathies. In one embodiment of the invention, the promoter is cell specific such that gene expression is restricted to red blood cells. Erythrocyte-specific expression is achieved by using the human β-globin promoter region and locus control region (LCR).

Retroviral vectors, including lentiviral vectors, of the invention optionally can also contain one or more elements that allow for the correct expression of the nucleic acid cassette, i.e. therapeutic gene of interest. In one embodiment of the invention, the gene of interest is a gene which is used to treat or reduce the detrimental effects of a hemoglobinopathic condition. Such genes include those encoding antisickling proteins that can be used to treat a hemoglobinopathy, wherein the antisickling protein is used to prevent or reverse the pathological events leading to sickling of erythrocytes in sickle cell conditions. For example, a globin gene, such as, β-globin, δ-globin, or α-globin gene, can be expressed using the retroviral vectors of the invention to treat hemoglobinopathies via gene therapy. In one embodiment, human β-globin is used to treat a subject who has a hemoglobinopathy, such as sickle cell disease or thalassemia.

Suitable β-globingenes for use in the present invention include wild-type and variant genes. In one embodiment, the β-globin gene is human $β^A$-globin gene. Variant β-globin genes include those genes which contain additions/deletions and mutant versions of the gene which have altered characteristics, including improved antisickling properties. In one embodiment, the β-globin gene comprises one or more deletions of intron sequences. In another embodiment, the β-globin is a mutant human β-globin gene encoding at least one anti sickling amino acid. Antisickling amino acids can be identified using standard alignment programs aligning β-globin with δ-globin and/or α-globin, thus deriving the antisickling amino acids from the δ-globin and/or α-globin protein sequences. In other embodiments, the human β-globin gene is the human $β^A$-globin gene encoding a threonine to glutamine mutation at codon 87 ($β^{A-T87Q}$).

One skilled in the art will recognize that the selection of the promoter to express the gene of interest will depend on the vector, the nucleic acid cassette, the cell type to be targeted, and the desired biological effect. One skilled in the art will also recognize that in the selection of a promoter the parameters can include: achieving sufficiently high levels of gene expression to achieve a physiological effect; maintaining a critical level of gene expression; achieving temporal regulation of gene expression; achieving cell type specific expression; achieving pharmacological, endocrine, paracrine, or autocrine regulation of gene expression; and preventing inappropriate or undesirable levels of expression. Any given set of selection requirements will depend on the conditions but can be readily determined once the specific requirements are determined. In one embodiment of the invention, the promoter is cell specific such that gene expression is restricted to red blood cells. Erythrocyte-specific expression is achieved by using the human β-globin promoter region and locus control region (LCR).

Standard techniques for the construction of expression vectors suitable for use in the present invention are well-known to those of ordinary skill in the art and can be found in such publications as Sambrook et al. (1989) *Molecular Cloning: A Laboratory Manual,* 2nd Ed. Cold Spring Harbor, N.Y. A variety of strategies are available for ligating fragments of DNA, the choice of which depends on the nature of the termini of the DNA fragments and which choices can be readily made by the skilled artisan.

Gene therapy vectors of the present invention, such as the foregoing retroviral vectors, including lentiviral vectors, can be used to express a variety of therapeutic proteins in transformed erythroid cells. In one embodiment, the gene of interest to be expressed in the vector is a gene which can be used to treat a hemoglobinopathy, such as the human β-globin gene or a variant thereof. Variants of human β-globin are described in the examples below, and include, for example, β-globin variants which include a substitution of threonine at position 87 with glutamine [$β^{487}$ Thr:Gln ($β^{A-T87Q}$)] The gene of interest can be obtained for insertion into the viral vector through a variety of techniques known to one of ordinary skill in the art.

Figure 1B:
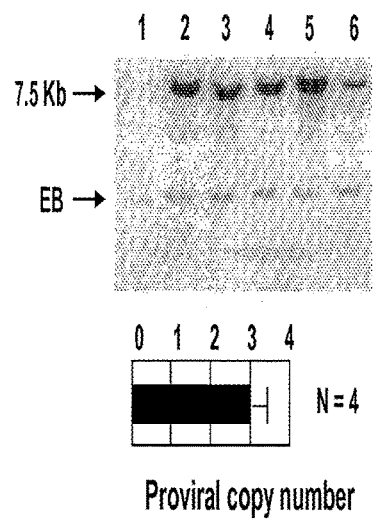
FIG. 1b shows a Southern blot analysis for proviral stability. Lane 1, NIH 3T3 negative control; lanes 2-4, bone marrow, spleen and thymus DNA, respectively, from a representative C57B1/6 recipient of A-T87Q-globin transduced bone marrow sacrificed 5 months post-transplantation; lanes 5 and 6, DNA from 2 day 12 spleen colonies generated using bone marrow from the primary C57B1/6 recipient sacrificed 5 months post-transplantation. The expected 7.5 Kb proviral band and a 3.2 Kb endogenous band (EB) are marked in the left margin. Bottom: average proviral copy number in genomic DNA isolated from blood of A-T87Q-globin transduced C57B1/6 mice 3 months post-transplantation (bar=SE). Quantification was performed by densitometry and comparison to NIH3T3 cells known to contain one copy of the provirus.
Figure 1C:
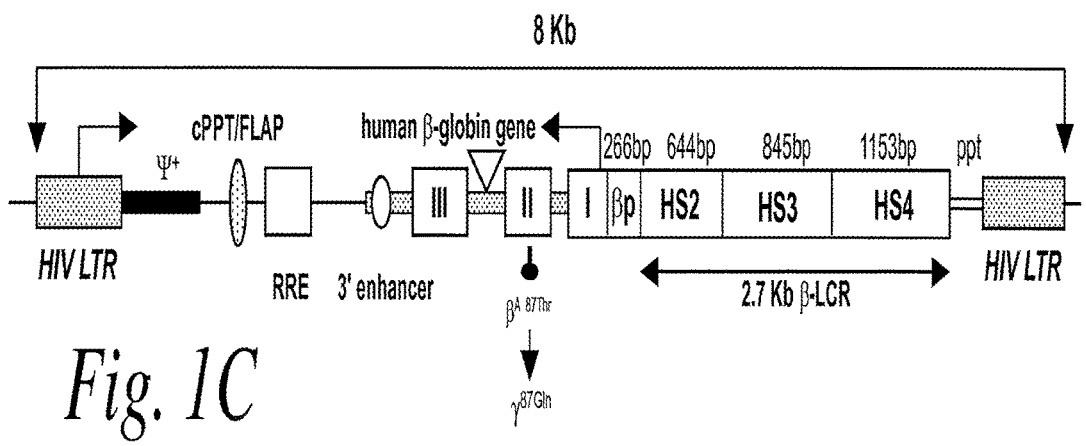
FIG. 1c graphically depicts the $β^{A-T87Q}$-globin provirus. HIV LTR, human immune deficiency type-1 virus long terminal repeat; ψ+, packaging signal; cPPT/flap, central polypurine tract/DNA flap; RRE, Rev-responsive element; βP, β-globin promoter (from SnaB I to Cap site); ppt, polypurine tract. The 3 'β-globin enhancer (up to downstream Avr II site), the 372 by IVS2 deletion, the $β^{A-T87Q}$ mutation (ACA Thr to CAG Gln) and DNase I hypersensitive sites (HS)2 (Sma I to Xba I), HS3 (Sac I to Pvu II) and HS4 (Stu I to Spe I) of the β-globin LCR are indicated.

Particular gene therapy vectors of the invention include, but are not limited to, the lentiviral vectors shown in FIG. 1c, FIG. 13, and FIG. 14. This HIV-based recombinant lentiviral vector contains, in a 5' to 3' direction, the 5' flanking HIV LTR, a packaging signal or ψ+, a central polypurine tract or DNA flap of HIV-1 (cPPT/FLAP), a Rev-response element (RRE), the human β-globin gene 3' enhancer, a gene of interest, such as the human β-globin gene variant containing the $β^{A87}$ Thr:Gln mutation, 266 by of the human β-globin promoter, 2.7 kb of the human β-globin LCR, a polypurine tract (PPT), and the 3' flanking HIV LTR. The LTR regions further comprise a U3 and U5 region, as well as an R region. The U3 and U5 regions can be modified together or independently to create a vector which is self-inactivating, thus increasing the safety of the vector for use in gene delivery. The U3 and U5 regions can further be modified to comprise an insulator element. In one embodiment of the invention, the insulator element is chicken HS4. cDNA of the therapeutic gene of interest, such as, for example, human β-globin, is amplified by PCR from an appropriate library. The gene is cloned into a plasmid, such as pBluescript II KS (+) (Stratagene), containing a desired promoter or gene-expression controlling elements, such as the human β-globin promoter and LCR elements. Following restriction enzyme digestion, or other method known by one skilled in the art to obtain a desired DNA sequence, the nucleic acid cassette containing the promoter and LCR elements and therapeutic gene of interest is then inserted into an appropriate cloning site of the lentiviral vector, as shown in FIG. 1c.

The step of facilitating the production of infectious viral particles in the cells may be carried out using conventional techniques, such as standard cell culture growth techniques. If desired by the skilled artisan, lentiviral stock solutions may be prepared using the vectors and methods of the present invention. Methods of preparing viral stock solutions are known in the art and are illustrated by, e.g., Y. Soneoka et al. (1995) *Nucl. Acids Res.* 23:628-633, and N. R. Landau et al. (1992) *J. Virol.* 66:5110-5113. In a method of producing a stock solution in the present invention, lentiviral-permissive cells (referred to herein as producer cells) are transfected with the vector system of the present invention. The cells are then grown under suitable cell culture conditions, and the lentiviral particles collected from either the cells themselves or from the cell media as described above. Suitable producer cell lines include, but are not limited to, the human embryonic kidney cell line 293, the equine dermis cell line NBL-6, and the canine fetal thymus cell line Cf2TH.

The step of collecting the infectious virus particles also can be carried out using conventional techniques. For example, the infectious particles can be collected by cell lysis, or collection of the supernatant of the cell culture, as is known in the art. Optionally, the collected virus particles may be purified if desired. Suitable purification techniques are well known to those skilled in the art.

Other methods relating to the use of viral vectors in gene therapy can be found in, e.g., Kay, M. A. (1997) *Chest* 111(6 Supp.):138S-142S; Ferry, N. and Heard, J. M. (1998) *Hum. Gene Ther.* 9:1975-81; Shiratory, Y. et al. (1999) *Liver* 19:265-74; Oka, K. et al. (2000) *Curr. Opin. Lipidol.* 11:179-86; Thule, P. M. and Liu, J. M. (2000) *Gene Ther.* 7:1744-52; Yang, N. S. (1992) *Crit. Rev. Biotechnol.* 12:335-56; Alt, M. (1995) *J. Hepatol.* 23:746-58; Brody, S. L. and Crystal, R. G. (1994) *Ann. N.Y. Acad. Sci.* 716:90-101; Strayer, D. S. (1999) *Expert Opin. Investig. Drugs* 8:2159-2172; Smith-Arica, J. R. and Bartlett, J. S. (2001) *Curr. Cardiol. Rep.* 3:43-49; and Lee, H. C. et al. (2000) *Nature* 408:483-8.

Retroviral vectors, including lentiviral vectors, as described above can be administered in vivo to subjects by any suitable route, as is well known in the art. The term "administration" refers to the route of introduction of a formulated vector into the body. For example, administration may be intravenous, intramuscular, topical, oral, or by gene gun or hypospray instrumentation. Thus, administration can be direct to a target tissue or through systemic delivery. Administration directly to the target tissue can involve needle injection, hypospray, electroporation, or the gene gun. See, e.g., WO 93/18759, hereby incorporated by reference herein.

Alternatively, the retroviral vectors of the invention can be administered ex vivo or in vitro to cells or tissues using standard transfection techniques well known in the art.

The retroviral vectors of the invention can also be transduced into host cells, including embryonic stem cells, somatic stem cells, or progenitor cells. Examples of progenitor host cells which can be transduced by the retroviral vectors of the invention include precursors of erythrocytes and hematopoietic stem cells. In another embodiment, the host cell is an erythrocyte. Transduced host cells can be used as a method of achieving erythroid-specific expression of the gene of interest in the treatment of hemoglobinopathies.

As used herein "pharmaceutically acceptable carrier" includes any and all solvents, dispersion media, coatings, antibacterial and antifungal agents, isotonic and absorption delaying agents, and the like that are physiologically compatible. In one embodiment, the carrier is suitable for parenteral administration. Preferably, the carrier is suitable for administration directly into an affected joint. The carrier can be suitable for intravenous, intraperitoneal or intramuscular administration. Pharmaceutically acceptable carriers include sterile aqueous solutions or dispersions and sterile powders for the extemporaneous preparation of sterile injectable solutions or dispersion. The use of such media and agents for pharmaceutically active substances is well known in the art. Except insofar as any conventional media or agent is incompatible with the active compound, use thereof in the pharmaceutical compositions of the invention is contemplated. Supplementary active compounds can also be incorporated into the compositions.

Another aspect of the invention pertains to pharmaceutical compositions of the lentiviral vectors of the invention. In one embodiment, the composition includes a lentiviral vector in a therapeutically effective amount sufficient to treat or prevent (e.g. ameliorate the symptoms of a hemoglobinopathy), and a pharmaceutically acceptable carrier. A "therapeutically effective amount" refers to an amount effective, at dosages and for periods of time necessary, to achieve the desired therapeutic result, such as treatment or prevention of a hemoglobinopathic condition. A therapeutically effective amount of lentiviral vector may vary according to factors such as the disease state, age, sex, and weight of the individual, and the ability of the lentiviral vector to elicit a desired response in the individual. Dosage regimens may be adjusted to provide the optimum therapeutic response. A therapeutically effective amount is also one in which any toxic or detrimental effects of the lentiviral vector are outweighed by the therapeutically beneficial effects. The potential toxicity of the lentiviral vectors of the invention can be assayed using cell-based assays or art recognized animal models and a therapeutically effective modulator can be selected which does not exhibit significant toxicity. In a preferred embodiment, a therapeutically effective amount of a lentiviral vector is sufficient to treat a hemoglobinopathy.

Sterile injectable solutions can be prepared by incorporating lentiviral vector in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

It is to be noted that dosage values may vary with the severity of the condition to be alleviated. It is to be further understood that for any particular subject, specific dosage regimens can be adjusted over time according to the individual need and the professional judgment of the person administering or supervising the administration of the compositions, and that dosage ranges set forth herein are exemplary only and are not intended to limit the scope or practice of the claimed composition.

The amount of viral vector in the composition may vary according to factors such as the disease state, age, sex, and weight of the individual. Dosage regimens may be adjusted to provide the optimum therapeutic response. For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

A major advantage of retroviral vectors, including lentiviral vectors, is that they are capable of integrating into the genome of a host cell and, therefore, enable long term expression of therapeutic proteins. Lentiviral vectors have been successfully used to deliver exogenous genes both in vitro and in vivo to a large variety of cell populations in several species, including neurons of the central nervous system (Naldini et al. (1996) *Proc. Natl. Acad. Sci. USA* 93:11382-11388), retinal cells (Miyoshi et al. (1997) *Proc. Natl. Acad. Sci. USA* 94:10319-10323), and pancreatic cells (Giannokakis et al. (1999) *Gene Ther.* 6:1545-1551).

The invention is further illustrated by the following examples which should not be construed as limiting.

EXAMPLES

Materials and Methods
Whole-Blood p50 Analysis

In the SCD mouse model experiments, p50 measurements on whole blood were performed using a Hemoscan (Aminco, Silver Spring, Md.). The concentration of deoxygenated HbS in equilibrium with the polymer (CSAT) was determined using the p50 method (R. E. Benesch et al. (1978) *Analytical Biochem.* 89:162) for various mixtures of HbS with test hemoglobins (1:1 ratio). p50 is the oxygen pressure at which half of the molecules of Hb are deoxygenated, as detected spectroscopically. Because the HbS polymer has a much lower oxygen affinity than HbS in solution, a sudden jump in p50 indicates the start of the formation of the polymer, and the concentration of Hb at which the jump occurs gives the CSAT value, expressed in g/dl Vector Construction and Virus Production The human beta-globin gene including its promoter and 3' enhancer sequence was cloned from BGT9 (Pasceri, et al. (1998) *Blood* 92:653). A 374 bp fragment was deleted from intron 2 and hypersensitive sites 2-4 were cloned from BGT33 (Rubin, et al. (2000) *Blood* 95:3242). Virus stocks were generated by transient transfection of 293T cells with the recombinant lentiviral vector together with separate plasmids expressing HIV-1 Gag-Pol, Rev and Tat. DNA sequence of the vector will be provided upon request. One liter of virus was concentrated by ultracentrifugation at 25,000 RPM for 90 minutes at 4° C. and the viral pellet resuspended in 300 ul of serum free medium (Life Technologies, Frederick, Md.). The absence of replication competent retrovirus (RCR) was verified by mobilization assay as described (Pawliuk, et al. (1994) *Blood* 84:2868). Viral titers were determined by Southern blot analysis.

RNA and DNA Analyses

In the SCD mouse model experiments, Southern blot analysis was performed using standard methods (Pawliuk et al., supra). A $^{32}$P-labeled exonic fragment of the human β-globin gene was used as a probe. Quantification of vector copy number was achieved by densitometry using a phosphoimager with ImageQua™ software (Molecular Dynamics, Sunnyvale, Calif.). DNA was digested with Afl II and probed with an exonic fragment of the human β-globin gene.

In the THAL experiments, human β globin RNA in peripheral reticulocytes was quantified by RNase protection assay as described in Leboulch et al. (1994) *EMBO* 13:3065. A 1.6-kb BamH1 fragment of the human β globin gene, [$^{32}$P]dCTP-labeled by random priming, was used as a probe.

THAL Mouse Model

β-Thalassemia mice homozygous for a deletion of the murine β-major gene (C57BL/6 Hbb$^{th}$-1/Hbb$^{th}$-1) (Skow et al. (1983) *Cell* 34:1043) hereafter referred to as THAL mice, and control C57BL/6(B6) mice were bred from parental stocks obtained from The Jackson Laboratory. The identity of homozygous THAL mice was confirmed by isoelectric focusing analysis of RBC lysates to detect characteristic single, slow-migrating Hb tetramers consisting of two murine a and two murine B minor globin chains.

Bone Marrow Transduction and Transplantation

In the SCD mouse model experiments, donor mice were injected 4 days before bone marrow harvest with 150 mg/kg of 5-fluorouracil (5-FU). Cells were prestimulated overnight in serum free medium (Life Technologies, Frederick, Md.) supplemented with 200 mM L-glutamine, 6 ng/ml of murine Interleukin-3, 10 ng/ml of human Interleukin-6, 10 ng/ml of murine Interleukin-1α and 100 ng/ml of murine Stem Cell Factor (Peprotech, Rocky Hill, N.J.). Cells were exposed to concentrated viral supernatants on Retronectin™ (Biowhittaker, East Rutherford, N.J.) coated plates for 5-6 hours in the presence of 8 μg/ml of protamine sulfate (Sigma, St. Louis, Mo.). Following infection, cells were harvested and injected, without selection, into recipient mice given 1100 cGy ($^{123}$Cs γ-rays) of total body irradiation (split dose of 550 cGy over 3 hours).

For experiments using THAL mice, bone marrow cells (24×10$^6$) from male THAL mice injected intravenously 4 days previously with 5-fluorouracil (100 mg/kg) were stimulated overnight in Iscove's medium supplemented with 1% BSA, 10 μg/ml bovine pancreatic insulin, and 200 μg/ml human transferrin (BIT; StemCell Technologies, Vancouver), 10$^{-4}$ M 2-mercaptoethanol, 2 mM glutamine, 10 ng/ml human interleukin-11 (IL-11, Genetics Institute, Cambridge, Mass.), 100 ng/ml human flt3-ligand (Immunex, Seattle, Wash.) and 300 ng/ml murine steel factor (expressed in COS cells and purified at the Terry Fox Laboratories, Vancouver). The next day, harvested cells were pelleted and resuspended in 0.9 ml of the aforementioned medium containing the same growth factor combination with concentrated, vesicular stomatitis virus glycoprotein-G-pseudotyped GFP- or β globin-lentivirus at a final virus concentration of $1.5 \times 10^9$ infectious units/ml (functional titer measured by Southern blot analysis of transduced NIH 3T3 cells). Infection was performed for 5 h on fibronectin (5 µg/cm$^2$, Sigma)-coated Petri dishes in the presence of 5 µg/ml protamine sulfate. After infection, $2 \times 10^6$ cells were transplanted, without selection, by i.v. injection into each female THAL recipient given 900 cGy (110 cGy/min 37 Cs γ-rays) of total body irradiation.

FACS Analysis

RBCs were washed in PBS, fixed, permeabilized and stained with an FITC-labeled monoclonal antibody that specifically recognizes human HbA (PerkinElmer Wallac, Norton, Ohio). Samples were analyzed on a FACScan flow cytometer (Becton Dickinson, San Diego, Calif.).

Primer Extension Analysis

In the SCD mouse model experiments, total RNA was extracted from 100-2001 of blood using TRIzol reagent (LifeTechnologies, Frederick, Md.). Primer extension was performed using the Primer Extension System-AMV Reverse Transcriptase kit (Promega, Madison, Wis.) according to the manufacturer's instructions. Primers for human $β^A$-globin [5'-CAGTAACGGCAG ACTTCTCCTC-3'] (SEQ ID NO:1) and mouse B$^{single}$-globin [5'-TGATGTCT-GTTTC TGGGGTTGTG-3 (SEQ ID NO:2) generate extension products of 90 bp and 53 bp respectively. Extension products were radioactively labeled by including $^{32}$P dCTP in the reaction mixture.

Reactions were performed using 1 µg of RNA and run on a denaturing 7% polyacrylamide gel. Radioactive bands were quantified by phosphoimager analysis. Measurements were corrected for the number of dCTP residues in human (Rubin et al., supra) and mouse (Papadea et al., supra) extension products.

Protein Analysis

In the SCD mouse model experiments, quantification of β-globin chains and Hb by HPLC was performed as described in Fabry et al. (1995) *Blood* 86:2419 and Papadea et al. (1996) *Clin. Chem.* 42:57.

RBC Sickling

In the SCD mouse model experiments, sickling of erythrocytes was studied as a function of PO2, from 0 to 150 mm Hg. Blood was diluted with PBS (340 mOsm) containing 5 mM glucose and 0.5 g/dl of bovine serum albumin. Cells were equilibrated with a mixture of air and nitrogen at the desired PO2, for 30 minutes at 37° C. in a rotary shaker, and fixed by the addition of 4% formaldehyde equilibrated at the same PO2 and temperature. The reversal of sickling was determined after incubation of the fully deoxygenated cell suspension by reoxygenation with air at 0° C. for one hour, prior to fixation with the formaldehyde solution equilibrated with air at 0° C. Proportions of sickle and non-sickle cells were determined by microscopy using Nomarski optics.

Hematology

In the SCD mouse model experiments, red cell counts and total Hb were measured on a CBC analyzer (CBC Technologies, Oxford, Conn.). Reticulocytes were analyzed using the Sysmex SE 9000 system (Sysmex Corp of America, Long Grove, Ill.).

Urine Concentrating Ability

In the SCD mouse model experiments, mice were deprived of water for 24 hours. At the end of this period, urine was collected onto Parafilm and the osmolarity measured after a 1:10 dilution with distilled water using a Microosmette (Precision Systems, Natick, Mass.).

RBC Density Gradients

In the SCD mouse model experiments, density gradients were performed as previously described in Fabry et al. (1991) *Blood* 78:217.

Delay Time of HbS Polymerization

In the SCD mouse model experiments, polymer formation upon deoxygenation of purified Hb or membrane free hemolysates was studied by measuring the delay time of polymerization with the method described by Adachi and Asakura (Adachi, et al. (1980) *J. Mol. Biol.* 144:467). In brief, after a temperature jump from 0° C. to 30° C. of the deoxygenated samples in a solution of 1.80 M potassium phosphate (pH 7.4) and 2 mM of sodium dithionite, the turbidity induced by HbS polymerization was recorded at 700 nm The probability factor for nucleation was derived from the measurement of the delay time performed at various Hb concentrations.

Globin Protein Analysis

In the THAL mouse experiments, the proportion of RBCs expressing human β globin protein was assessed by fluorescence-activated cell sorter (FACS) analysis of RBCs that had been fixed and stained with a biotinylated anti-human antibody (Perkin-Elmer) and Streptavidin-PE as described in Kalberer et al. (2000) *PNAS* 97:5411. RBC lysates from freshly collected blood were analyzed by isoelectric focusing by using the Resolve Hb test kit (Perkin-Elmer) as described in Fabry et al. (1992) *PNAS* 89:12155. The globin composition was determined by HPLC with a denaturing solvent that separates the globin chains and a Vydac large-pore (3,000 A) C$_4$ column with a modified acetonitril/H$_2$O/trifluoroacetic acid gradient as described in Fabry et al., supra. The amount of unpaired α globin chains associated with RBC membranes was determined by urea Triton-polyacrylamide gel electrophoresis analysis as described in Rouyer-Fessard et al. (1989) *J. Biol. Chem.* 264:19092. In brief, after extensive washing of membrane ghosts, loading of equivalent amounts of protein, and Coomassie blue staining of the gel, proteins were analyzed by densitometry at 570 nm. The proportion of membrane-associated a globin chain was expressed as a percentage of total membrane proteins.

Hematologic Parameters and RBC Density Gradient

In the THAL mouse experiments, blood from the tail vein was used to analyze RBC indices and reticulocyte counts by using the Sysmex SE 9500 system (Sysmex Corp. of America, Long Grove, Ill.). Blood smears were stained with methylene blue for manual reticulocyte counts to validate the Sysmex reticulocyte counts in the majority of cases and these numbers correlated well. Blood smears were also stained with Wright-Giemsa by using an automatic stainer. Smears were reviewed blinded by two independent hematologists. RBC densities were examined on Percoll-Larex gradients (Larex International, St Paul), as described in Fabry et al. (1984) *Blood* 90:3332. The Student's t test was used to determine whether hematological parameters differed between treatment groups.

Histopathology

In the THAL mouse experiments, livers and spleens were fixed in 10% neutral buffered formalin. Tissues were paraffin-embedded. Five-micrometer sections were stained with hematoxylin-eosin and Perls iron stain and subsequently examined by light microscopy.

Example I: Construction of Human β$^A$-Globin Gene Variant

In order to take advantage of the fact that γ-globin is a strong inhibitor of HbS polymerization, the human β$^A$-globin gene was mutated in such a way as to emulate the antisickling activity of γ-globin. A human β$^A$-globin gene variant was mutated at codon 87 to encode a Glutamine [β$^{A87}$ Thr:Gln (β$^{A-T87Q}$)], which is thought to be responsible for most of the antisickling activity of γ-globin (Nagel et al. (1979) *PNAS USA* 767:670).

In order to study the antisickling capacity and oxygen-binding affinity of the human β$^A$-globin gene variant, transgenic mice were made which expressed both human β$^{A-T87Q}$ and α-globins, but neither mouse α- nor mouse β-globin. These mice had normal hematological parameters and viability, and the β$^{A-T87Q}$-globin variant extracted from the RBCs was found to be almost as potent an inhibitor of HbS polymerization as γ-globin in vitro and much more so than β$^A$-globin, as shown in FIG. 1a. FIG. 1a shows that HbA-T87Q and HbF are potent inhibitors of HbS polymerization in vitro in contrast to HbA. As shown in FIG. 1a, whole blood analysis of p50, the pO$_2$ at which 50% of the Hb molecules are oxygenated, showed that the oxygen-binding affinity of β$^{A-T87Q}$ Hb was well within the range observed with wild-type β$^A$ Hb in mice: 31.1±0.2 mm Hg (standard error=SE) versus 32.7±1.8 mmHg (SE), respectively.

The β$^{A-T87Q}$-globin variant was then inserted in a lentiviral vector which was optimized for transfer to HSCs and erythroid-specific expression. The central polypurine tract/DNA flap of HIV-1 (Zennou et al. (2000) *Cell* 101:173) was incorporated in the construct to increase viral titers and transduction of HSCs after pseudotyping with the vesicular stomatitis virus glycoprotein G (VSV-G) and concentration, as shown in FIG. 1c. Southern blot analysis (FIG. 1b) showed titers reaching 1.5×10$^9$ infectious units per ml after pseudotyping with Vesicular Stomatitis Virus glycoprotein-G (VSV-G) and physical concentration. Specific LCR elements were chosen on the basis of results of single integrants in erythroid cells assessed by recombinase-mediated cassette exchange (Bouhassira et al. (1997) *Blood* 90:3332).

Example II: Analysis of β$^{A-T87Q}$-Globin Lentivirus

Figure 2A:
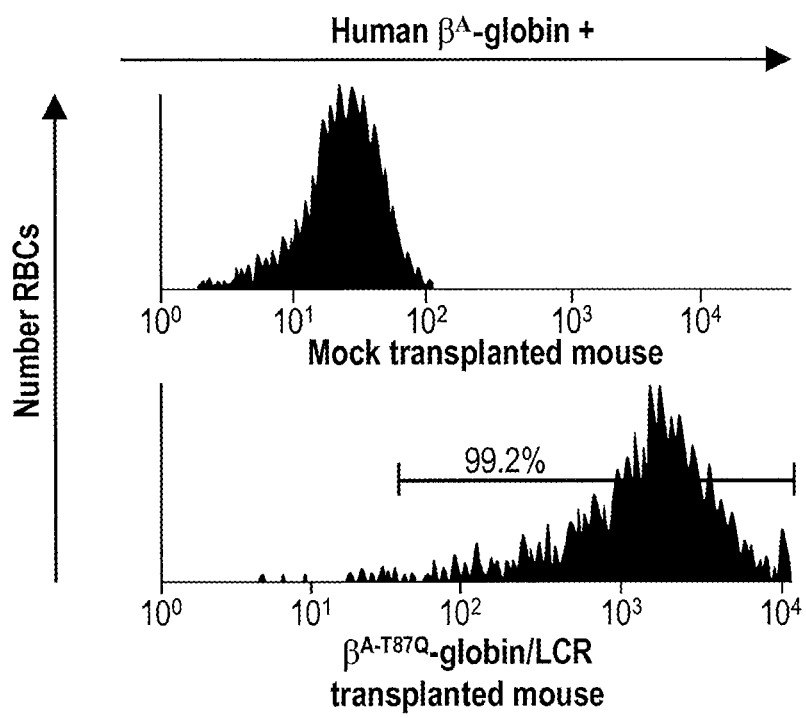
FIGS. 2a-2c graphically depict results from an analysis of human $β^{A-T87Q}$-globin gene expression in C57BL/6 recipient mice 5 months after transplantation.
Figure 2B:
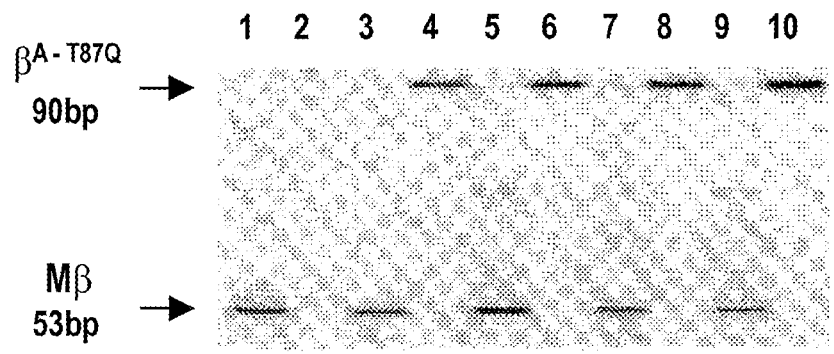
Figure 2C:
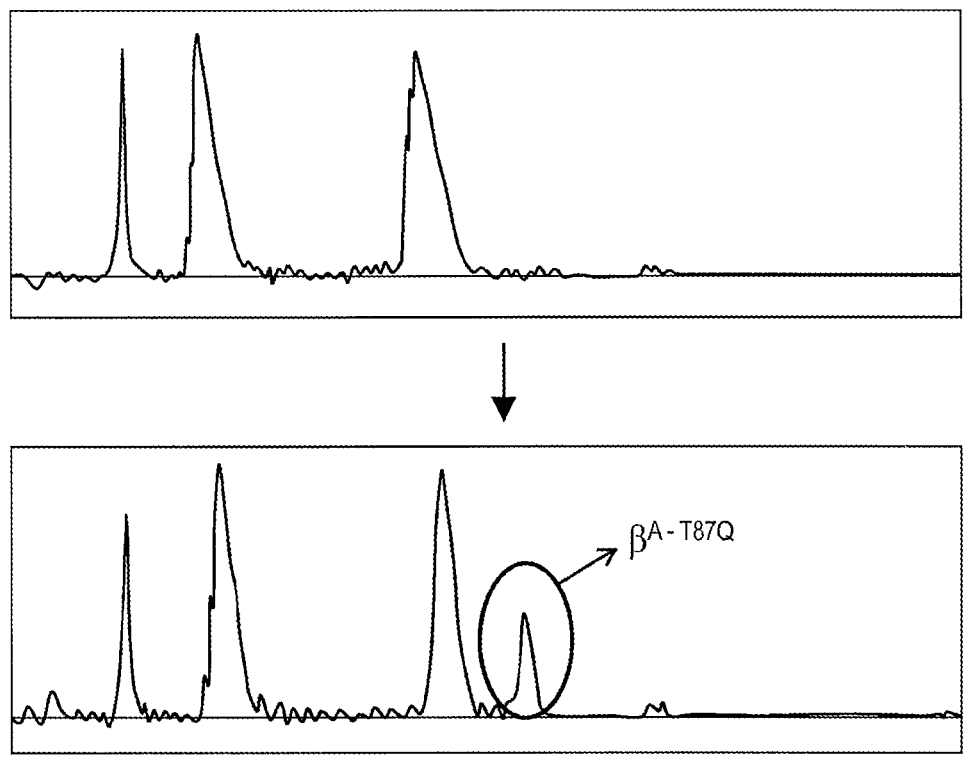

The β$^{A-T87Q}$-globin lentivirus was first analyzed in lethally irradiated normal syngeneic C57BL/6 recipient mice in the absence of any selection. Proviral transfer was stable with an average copy number of 3.0±0.5 (SE) per genome of peripheral nucleated blood cells 3 months after transplantation, as shown in FIG. 1b. At 10 months after transplantation, all mice expressing human β$^{A-T87Q}$-globin protein with up to 99% (mean 96±0.9% (SE)) of their RBCs staining positive with an antibody that specifically recognizes human β-globin, in this case, the β$^{A-T87Q}$ variant (FIG. 2a). No β$^{A-T87Q}$-globin expression was detected in other blood lineages by antibody staining Human β$^{A-T87Q}$-globin protein represented up to 22.5% [mean 16+3.1% (SE)] of endogenous mouse β-chains in recipients of β$^{A-T87Q}$-globin lentivirus-transduced bone marrow, as determined by high-performance liquid chromatography (HPLC) (FIG. 2c). The fourfold discrepancy between human β$^{A-T87Q}$-globin mRNA and protein levels is consistent with differences observed in mice transgenic for the β$^A$-globin gene (Alami et al. (1999) *Blood Cells Mol. Dis.* 25:110).

Long term secondary transplants were also performed with bone marrow from a representative primary recipient killed 5 months after transplantation. Fluorescence-activated cell sorting (FACS) analysis of peripheral blood samples of secondary recipients 4 months after transplantation showed that 87±2.3 (SE) of RBCs expressed high levels of human β$^{A-T87Q}$-globin protein, thus demonstrating that transduction of true HSCs was achieved. Analysis of position effect variegation suggested that pan-cellular expression was the result of balanced expression from polyclonal stem cell reconstitution with multiple chromosomal integration sites rather than true position-independent expression.

Example III: Gene Therapy of Mouse Models Using Retroviral Vectors

In Vivo Analysis of β$^{A-T87Q}$-Globin Lentivirus

In order to study the efficacy of the β$^{A-T87Q}$-globin lentiviral vector in vivo, two different SCD transgenic mouse models were used: SAD (Trudel et al. (1991) *EMBO J.* 10:3157) and Berkeley (BERK) (Paszty et al (1997) *Science* 278:876). SAD mice express human α-globin together with a "super S" globin resulting from two point mutations added to the human β$^S$ gene (Trudel et al., supra), whereas BERK mice, which express human α- and human β$^S$-globulins, do not express any murine globins because of complete disruption of both mouse α- and β-globin gene loci (Paszty et al., supra). The phenotype of BERK mice is overall more severe than that of SAD mice, although some of the hematological abnormalities in BERK mice are caused by an associated β-thalassemic syndrome due to suboptimal expression of the transgenic human β$^S$ gene (Nagel et al. (2001) *Br. J. Haematol.* 112:19).

SAD and BERK bone marrow was transduced with the β$^{A-T87Q}$-globin lentiviral vector and transplanted into lethally irradiated syngeneic C57BL/6 mouse recipients. Transduced SAD marrow was also transplanted into lethally irradiated syngeneic SAD recipients. Three months after transplantation, reconstitution of recipient C57BL mice with donor BERK or SAD bone marrow was essentially complete for all mice, as determined by quantification of murine β-single Hb by HPLC (FIG. 3).

Figure 4:
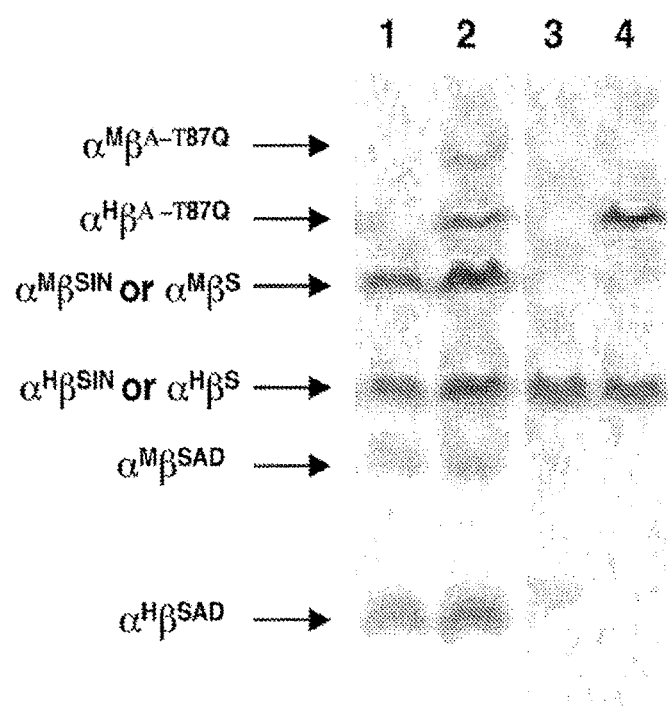
FIG. 4 shows isoelectric focusing of RBC lysates from recipient mice 3 months post-transplantation showing the expected species of Hb. Lanes 1 and 2, blood deriving from SAD transplanted marrow; lanes 3 and 4, blood deriving from BERK transplanted marrow; lanes 1 and 3, mock transduction; lanes 2 and 4, transduction with βA-T87Q_globin lentivirus. $α^M$, mouse α-globin; $α^H$, human α-globin; $β^{SIN}$, mouse single β-globin; $β^{SAD}$, human SAD β-globin; $β^S$, human sickle β-globin; $β^{A-T87Q}$, human $β^{A-T87Q}$ globin.

Isoelectric focusing electrophoresis of blood samples from mice 3 months after transplantation shows all of the expected species of Hb, as shown in FIG. 4. The amount of β$^{A-T87Q}$-globin expressed in the transplanted mice, as measured by Hb HPLC, was up to 108% (mean 75.5±17.1% (SE)) and 51% (mean 42.5±5.5% (SE)) of the transgenic HbS for recipients of β$^{A-T87Q}$-globin lentivirus-transduced BERK and SAD bone marrow, respectively, as shown in FIG. 3. These values correspond to up to 52% and 12% of the total Hb of BERK and SAD mice, respectively. The greater amount of ≈$^{A-T87Q}$-globin-containing Hb observed in erythrocytes derived from transduced bone marrow cells of BERK mice as compared to SAD mice may be explained by the absence of the murine β-globulin mRNA and the associated thalassemic phenotype of BERK mice, which favors translation of the added β$^{A-T87Q}$ globin mRNA species (Nagel et al, supra, 2001).

In Vivo Analysis of Polymerization Inhibition

Figure 5A:
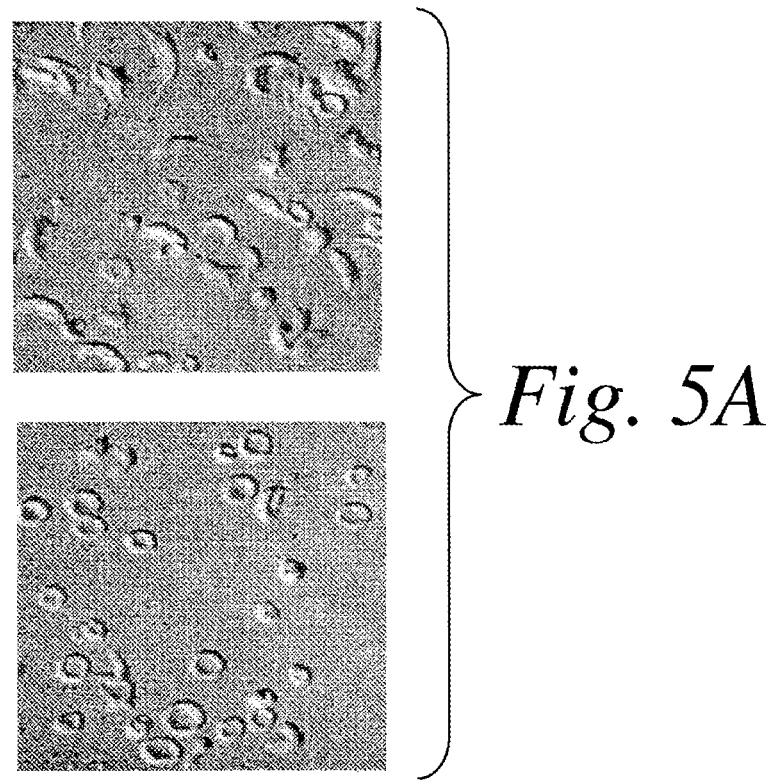
FIGS. 5a-5e show correction of SCD pathology.
Figure 5B:
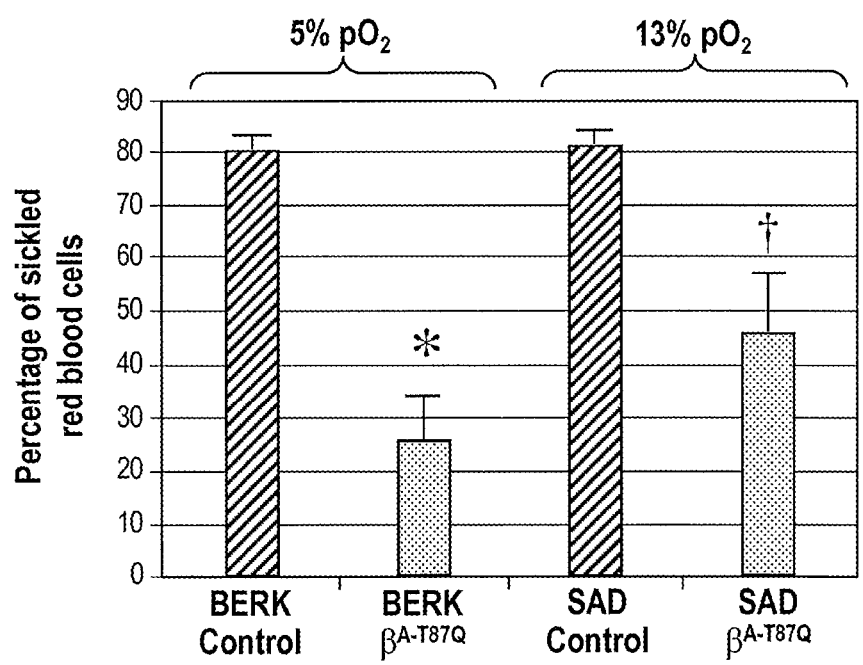

In order to determine whether β$^{A-T87Q}$-globin was capable of inhibiting HbS polymerization in vivo in transplanted SCD mouse models, the morphology of RBCs from transplanted mice was analyzed as a function of oxygen pressure in vitro. Examination of the obtained sigmoid sickling curves showed a marked change in the proportion of sickled cells, as shown in FIGS. 5a and 5b. For recipients of β$^{A-T87Q}$-globin lentivirus-transduced BERK marrow, the greatest difference occurred at 5% pO$_2$, with 80±1.7% (SE)

versus 26±7.5% (SE) (P=0.01) sickle cells for mock-transduced and $\beta^{A\text{-}T87Q}$-globin lentivirus-transduced marrow, respectively. In comparison, analysis of RBCs from humans with sickle trait, who are heterozygous for the $\beta^S$ allele and asymptomatic, showed ~40% sickled cells at 5% pO$_2$, with 81±3% (SE) versus 46±11% (SE) (P=0.03) sickle cells for mock-transduced and $\beta^{A\text{-}T87Q}$-globin lentivirus-transduced marrow, respectively. Examination of peripheral blood smears at ambient pO2 showed an eightfold decrease in the proportion of irreversibly sickled cells (ISCs) in mice transplanted with $\beta^{A\text{-}T87Q}$-globin lentivirus-transduced BERK marrow with complete disappearance of highly dehydrated ISCs. For SAD mice, no ISCs could be detected after $\beta^{A\text{-}T87Q}$-globin lentivirus-transduction, as shown below in Table 1. Table 1 shows the correction of hematological abnormalities and urine concentrating defect in recipients of $\beta^{A\text{-}T87Q}$-globin-transduced BERK bone marrow.

In Vivo Analysis of SCD-Associated Symptoms

The amelioration of SCD-associated splenomegaly and characteristic urine concentration defect in BERK mice was examined using gene therapy. Following transplantation of $\beta^{A\text{-}T87Q}$-globin lentivirus-transduced BERK marrow, both pathological features were corrected, whereas no effect was observed for recipients of mock-transduced BERK marrow (Table 1 and FIG. 5e).

Example IV: Analysis of Position Effect Variegation

In order to determine whether the observed pancellular expression of human A-T87Q-globin protein in RBCs was the result of position-independent expression of the transferred A-T87Q-globin gene, bone marrow from a representative primary C57B1/6 recipient sacrificed 5 months post-transplantation was used to generate day 12 spleen colonies

TABLE 1

Correction of hematological abnormalities and urine concentrating defect in recipients of $\beta^{A\text{-}T87Q}$-globin-transduced BERK bone marrow

| Mice* | RBCs (10$^6$/μl) | Hb (g/dl) | Reticulocytes (%) | ISCs † (%) | Urine concentrations (mOsM) (number of mice) |
|---|---|---|---|---|---|
| C57BL/6 controls (n = 3) | 10.1 ± 0.3 | 15.0 ± 0.6 | 4.1 ± 0.6 | — | 3247 ± 500 (n = 22) |
| BERK controls (n = 3) | 7.4 ± 0.6 | 9.4 ± 0.9 | 17.8 ± 0.6 | 16.0‡ | 1452 ± 331 (n = 4) |
| BERK $\beta^{A\text{-}T87Q}$ (n = 3) | 10.1 ± 1.1§ | 13.0 ± 0.4‖ | 5.8 ± 1.8¶ | 2.0 # | 3600 ± 381 (n = 2)** |
| SAD control (n = 4) | 8.4 ± 0.6 | 13.0 ± 0.6 | 3.4 ± 1.2 | 2.6 # | 3840 ± 175 (n = 3) |
| SAD $\beta^{A\text{-}T87Q}$ (n = 3) | 8.7 ± 0.1 | 13.7 ± 0.2 | 2.8 ± 0.1 | 0 | 3920 ± 326 (n = 3) |

RBCs, red blood cells; Hb, hemoglobin; ISCs, irreversibly sickled cells.
Values shown with SE and statistical significance established by Student's t test.
*n is the number of mice for RBCs, Hb, and reticulocytes.
† A total of 2000 RBCs were examined from BERK control and BERK $\beta^{A\text{-}T87Q}$ mice (n = 2) and 3000 RBCs were examined from SAD control and SAD $\beta^{A\text{-}T87Q}$ mice (n = 2).
§P = 0.15 with substantial correction of anisocytosis and poikilocytosis.
‖P = 0.01.
¶P = 0.05.
Only hydrated ISCs.
‡Mostly dehydrated ISCs.
**P = 0.01.

Figure 5C:
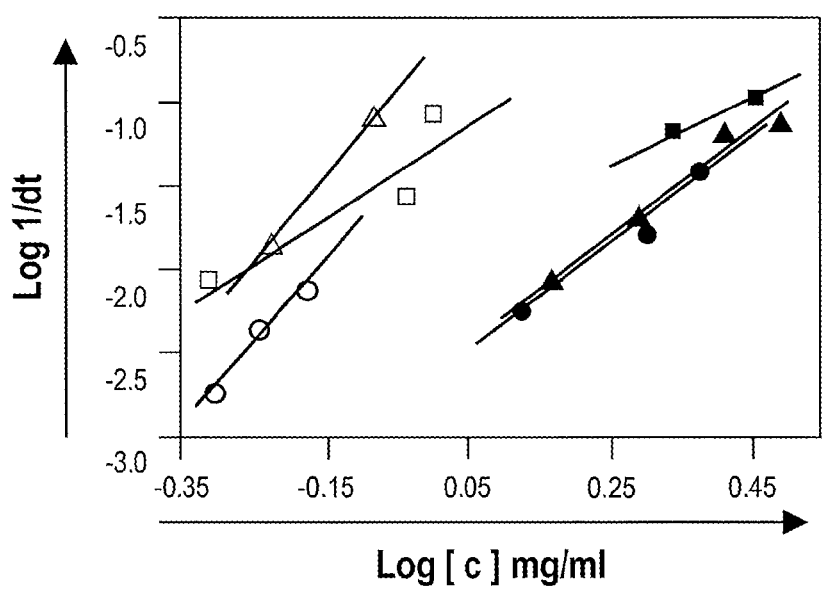

Kinetic studies of HbS polymer formation by turbidimetry of RBC lysates from transplanted mice showed delayed HbS polymerization in lysates from mice transplanted with either SAD or BERK marrow transduced with either SAD or BERK marrow transduced with the $\beta^{A\text{-}T87Q}$-globin lentivirus (FIG. 5c). The change in kinetics paralleled what was observed with RBC lysates from homozygote SS patients versus asymptomatic AS heterozygotes.

Figure 5D:
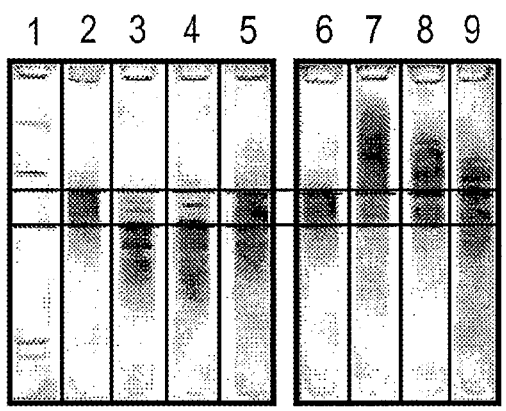
Figure 5E:
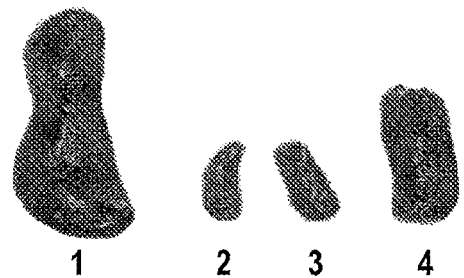

The density of RBCs from transplanted SCD mouse models were examined since HbS polymerization causes abnormally high cell density (Blouin et al., supra; Nagel el al., supra, 2001). Whereas RBCs from control and mock-transduced SAD mice had a higher density than those of syngeneic C57BL/6 mice, mice completely reconstituted with $\beta^{A\text{-}T87Q}$-globin lentivirus-transduced SAD marrow showed a clear shift toward normal (FIG. 5d). In BERK RBCs, the phenomenon was reversed, because the associated thalassemic phenotype decreases the mean corpuscular Hb concentration, resulting in lower cell density. The addition of $\beta^{A\text{-}T87Q}$-globin partially cured the thalassemia and resulted in higher cell density, as shown in FIG. 5d.

Unlike SAD mice, BERK mice have major alterations of their hematological parameters, as a consequence of both SCD and the associated thalassemia (Nagel et al., supra, 2001; Paszty et al., supra). In mice transplanted with $\beta^{A\text{-}T87Q}$-globin lentivirus-transduced BERK marrow, RBC and reticulocyte counts were corrected with amelioration of Hb concentration, anisocytosis, and poikilocytosis (Table 1).

in secondary recipient mice. Southern blot analysis was performed on genomic DNA isolated from 20 individual spleen colonies following digestion with BamH I, which cuts only once within the integrated provirus. Ten distinct clones were observed with an average proviral copy number of 3.4±0.3 (SE) (range 2-5). Primer extension analysis of mRNA from spleen colonies showed a wide variation in the amount of human A-T87Q-globin mRNA. These results suggest that pancellular expression was the result of balanced expression from polyclonal stem cell reconstitution with multiple chromosomal integration sites rather than true position-independent expression.

In summary, the previous examples demonstrate that chromosomal integration of an antisickling globin gene variant in HSCs can result in its pancellular, erythroid-specific expression at levels sufficiently high to correct the main pathological features of SCD. The previous examples also demonstrate that structural optimization of the $\beta^{A\text{-}T87Q}$-globin gene/LCR lentivirus by recombination-mediated cassette exchange and incorporation of the central polypurine tract-DNA flap of HIV-1, resulted in very high viral titers yielding multiple events of chromosomal integration per hematopoietic stem cell. This integration led to balanced expression which was sufficiently high and homogenous enough to provide an overall protection similar to that observed in asymptomatic human AS heterozygotes.

Example V: In Vivo Analysis of Gene Therapy in Thalassemia Mouse Model

In order to test the therapeutic efficacy of a lentiviral vector for the treatment of other hemoglobinpathies, the lentiviral vector containing wild-type human β globin gene was injected into the bone marrow of THAL mice, a murine model used for studying β thalassemia. THAL mice bear a homozygous deletion of the mouse β major gene and manifest a hypochromic, microcytic anemia with considerable anisocytosis, poikilocytosis, reticulocytosis, the presence of inclusion bodies in a high proportion of their circulating RBCs, and abnormally dehydrated erythrocytes (Skow et al. (1983) *Cell* 34:1043).

Figure 14A:
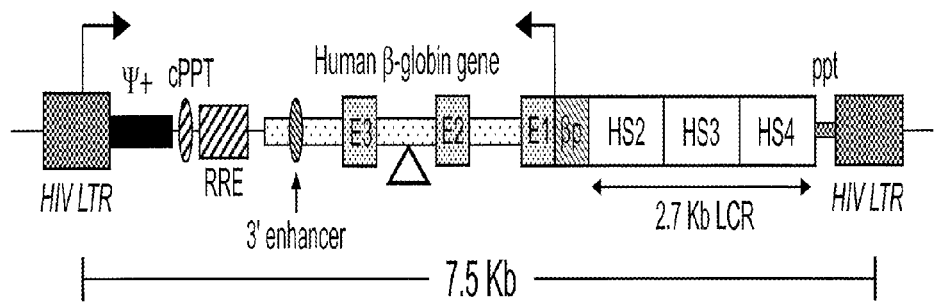
FIGS. 14a-14c show a diagram of a lentiviral vector containing the human β-globin gene and results demonstrating successful expression of the human β globin gene in mice.

The lentiviral globin gene vector used in the experiments is schematically shown in FIG. 14A. This vector is based on the design previously described in detail above and proven successful for the correction of sickle cell disease, except that it now incorporates the wild-type human β globin gene. The lentiviral vector notably contains specific segments of promoter and LCR of the gene of interest, i.e., human β globin, and also incorporates the central polypurine tract/DNA flap of HIV-1.

Recombinant virus pseudotyped with vesicular stomatitis virus glycoprotein-G was produced and subsequently concentrated 1,000-fold by two rounds of ultracentrifugation as described above and in Pawliuk et al. (2001), supra. A lentiviral vector carrying the gene that encodes enhanced GFP driven by the elongation factor 1-α promoter was also generated and used as a control in some of the following experiments. The absence of replication competent virus was verified by mobilization assay. Viral titers were determined functionally by quantitative Southern blot analysis of transduced NIB 3T3 cells with proviral copy number controls.

As shown in FIG. 14A, the vector contains HIV LTR, HIV type-1 long terminal repeat; $\psi_+$, packaging signal; cPPT, central polypurine tract/DNA flap; RRE, Rev-responsive element; E, exon; IVS, intervening sequence; βP, β globin promoter (from SnaBI to Cap site); HS, hypersensitive site; ppt, polypurine tract. The 3' β globin enhancer (up to downstream AvrII site), the 372-bp IVS2 deletion (indicated by the triangle) and DNase I hypersensitive sites, HS2 (SmaI to XbaI), HS3 (Sad to PvuII) and HS4 (StuI to SpeI) of the LCR.

The [β globin gene/LCR] lentiviral vector was optimized for viral titers and β globin gene expression by choosing specific segments of the β globin gene, its promoter, and the β-LCR on the basis of results of transgenic mouse experiments with single integrated copies and recombination-mediated cassette exchange (Bouhassira et al. (1997) *Blood* 90:3332) at the same sites of chromosomal integration in erythroid cell lines. In addition, the vector contains the HIV-1 central polypurine tract/DNA flap for increased transduction efficiency, as shown in FIG. 14A. After transient production in 293T cells on cotransfection with a plasmid encoding the pseudotyping vesicular stomatitis virus glycoprotein-G envelope and subsequent concentration by ultracentrifugation, the [β globin gene/LCR] lentiviral vector reached functional titers of $1.5 \times 10^9$ infectious units/ml, as assessed by Southern blot analysis of transduced NIH 3T3 cells with proviral copy number controls. The titers achieved were only 5-fold lower than those obtained with a similar lentiviral vector containing only the GFP gene driven by the elongation factor 1-α promoter.

In sum, the lentiviral vector incorporated several elements to enable production of stable, high-titer virus including a central polypurine tract/DNA flap element and rev-responsive element of HIV. After concentration, viral preparations with titers exceeding $10^9$/ml were achieved with a vector carrying an unmodified human β globin gene and extensive regions of the locus control region (LCR) including elements of HS2, 3, and 4 without any evidence of viral instability through abnormal splicing. The subsequent infection of murine bone marrow cells at high MOI resulted in essentially 100% gene transfer to repopulating cells with multiple proviral integrations per transduced cell.

Figure 14B:
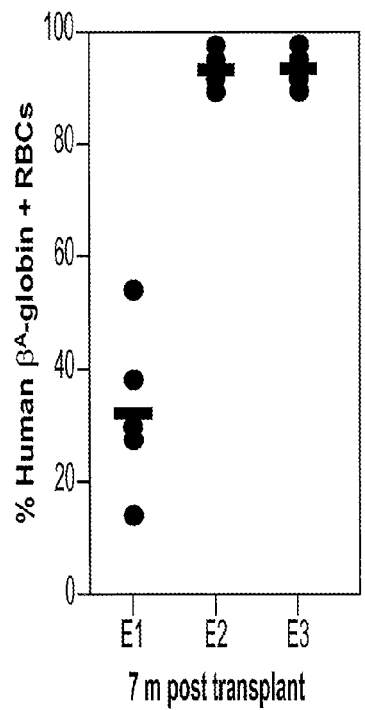
Figure 14C:
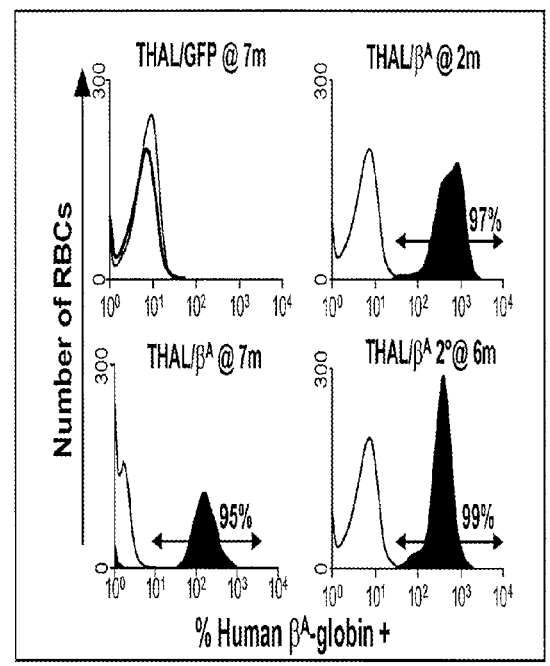

Persistent Panerythroid Expression of Lentivirus-Encoded Human 13 Globin in THAL Mice In order to ensure that β globin gene expression was persistent in murine RBCs, FACS analysis was performed. FIG. 14B shows the results of FACs analysis, with an antibody specific for human β globin chain, of peripheral blood RBCs of lethally irradiated THAL mice transplanted 7 months previously with syngeneic THAL bone marrow cells transduced with either the [β globin/LCR] or the control GFP lentiviral vector as described above. The proportion of peripheral blood RBCs expressing human β globin was assessed by FACS after staining the cells with an antibody specific for human β globin. RBCs were from THAL mice transplanted 7 months previously with bone marrow exposed to the lenti-β globin vector. The viral titer used in experiment 1 (E1), was about $2 \times 10^8$ infectious units/ml and in experiments 2 and 3 (E2, E3) was about $1.5 \times 10^9$ infectious units/ml. In all mouse recipients of cells transduced with the high-titer [β globin/LCR] vector preparations, about 95% of RBCs were positive for human β globin protein (FIG. 14B). The high-level reconstitution obtained with the high viral titer preparations was associated with a mean proviral copy number of about 3 per transduced cell, as assessed by Southern blot analysis of bone marrow, thymus, and spleens with proviral copy number controls. Time-course FACS analyses showed that reconstitution of the mice with human β globin+ RBCs was rapid, with pancellular expression observed as early as 2 months after transplant, and stable thereafter, even in THAL mice secondarily transplanted with marrow cells harvested from the primary THAL recipients (shown in FIG. 14C).

Similar transplantation experiments with a lower titer viral preparation ($2 \times 10^8$ infectious units/ml) resulted in a lesser proportion of RBCs expressing human β globin, indicating incomplete transduction of donor HSCs and position effect variegation of cells with a single integrated copy (FIG. 14B). In summary, the human p globin was successfully and persistently expressed in murine RBCs using the [β globin gene/LCR] lentiviral vector.

In Vivo Correction of a Globin Imbalance in THAL Mice Using Lentiviral Vector

Expression of therapeutic levels of human β globin in the THAL mice resulted in correction of the α globin protein imbalance in these mice. Human β globin protein constituted on average 32.4±4% (27-39%) of all β globin chains in RBC lysates of THAL mice in which anemia was corrected by transplantation, which was further supported by the results of isoelectric focusing analyses of blood samples from the transplanted THAL mice. Quantification of human $β^A$ was performed by HPLC according to standard protocols. An additional Hb species was documented in all corrected mice, consistent with the presence of Hb tetramer containing two murine α and two human β globin chains. Isoelectric focusing of RBC lysates from transplanted primary mice showing the expected species of Hb with two murine α and two human β chains. Lanes 1-4, primary recipients; lanes 5 and 6, secondary recipients of lenti-β globin-transduced THAL bone marrow cells. Quantification of human β globin RNA in peripheral blood cells by RNA protection assay showed up to 130% levels relative to total mouse a globin RNA. As previously observed, human β globin protein levels represent only a fraction of those of the encoding RNA, presumably because of intrinsic differences in association constants between mouse and human globin chains to form Hb tetramers and/or differential competition for globin translation between human and mouse mRNA species (Alami et al. (1997) *Blood Cells Mol Dis* 25:110).

The transplanted THAL mice also had complete clearance of the excess of membrane-bound a globin chains, which represent about 1% of RBC membrane-associated proteins in normal mice (1.4±0.7% in corrected THAL mice versus 15.3±1% in GFP transplanted THAL controls).

Figure 15:
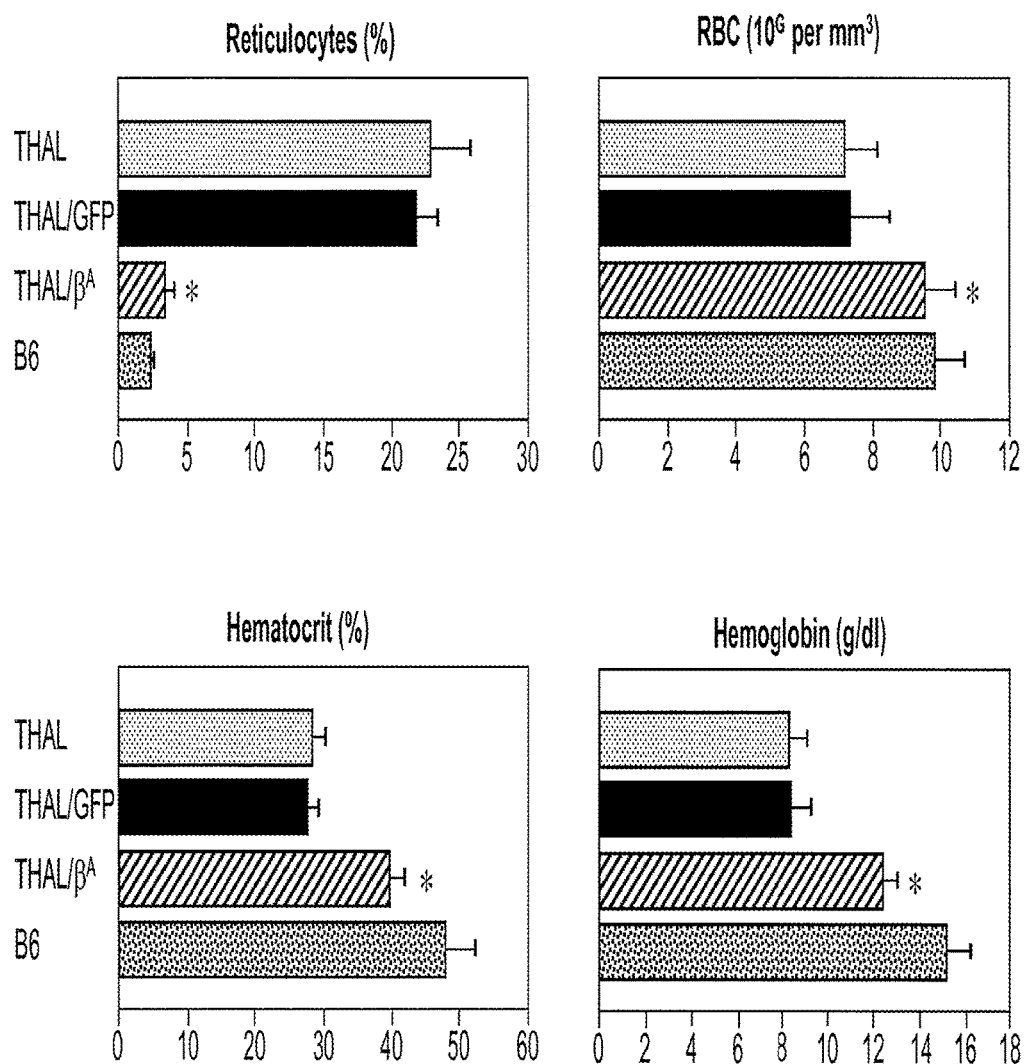
FIG. 15 shows improvement of hematological parameters in THAL mice who received lenti-β globin-transduced THAL bone marrow cells. Results shown are the mean±SD for untransplanted, control THAL mice (n=5), normal unmanipulated B6 mice (n=5), and THAL mice transplanted 6 months previously with lenti-β globin-transduced cells (n=8) or control lenti-GFP-transduced cells (n=6). Changes in all hematologic parameters seen in THAL recipients of lenti-β globin-transduced cells were highly significant in comparison with nontransplanted, or control (GFP)-transplanted THAL mice (*, P<0.001). Values for the RBC number and reticulocyte count in these corrected mice reached levels within the normal range of control B6 mice (P=0.6 and 0.1, respectively).

In Vivo Expression of Human 13 Globin in THAL Mice Corrects Hematologic Parameters and Abnormal RBC Morphology in Lentiviral Recipients THAL mice showing pancellular erythroid expression of human β globin showed a marked improvement in all RBC indices, including decreased reticulocyte percentage, increased RBCs, increased hematocrit percentage, and increased Hb (FIG. 15). Compared with pretransplant values, significant elevations (P<0.001) occurred in RBC number (from $7 \times 10^6$ to $9.7 \times 10^6 \pm 0.9$ per mm3), hematocrit (from 28 to 40±2.3%), and Hb concentration (from 8 to 12.4±0.7 g/dl) with RBC levels rising to within the normal range (no significant difference compared with normal, unmanipulated B6 mice) and just under normal levels for the hematocrit and Hb concentration. This correction of anemia was further reflected in a dramatic reduction in reticulocyte numbers from levels of >20% to 3.4±0.8%, again reaching the normal range. No improvement occurred in any parameters when THAL mice were transplanted with bone marrow transduced with a GFP control vector' as shown in FIG. 15.

In addition, histologic analysis was performed on the lentiviral and control THAL mice to further examine the morphology associated with the improved hematologic parameters. Findings from morphologic examination of blood smears were consistent with the observed hematological improvements. Blood smears of experimental and control animals demonstrated that correction of the anemia characteristic of THAL mice was associated with a marked reduction in RBC anisocytosis, poikilocytosis, and polychromasia. More than 75% of the RBCs were normochromic and normocytic in both primary and secondary recipients. Control mice transplanted with lenti-GFP virus-transduced bone marrow cells remained severely anemic with marked reticulocytosis and maintained their abnormal red cell morphology.

To assess further the correction of the anemia, RBC density analyses were performed. Thalassemic RBCs have a decreased mean hemoglobin concentration and correspondingly lower density as compared with normal RBCs (Fabry et at (1984) (supra). In THAL recipients of [β globin gene/LCR] lentivirus-transduced marrow, the density of RBCs narrowed dramatically toward the normal range. In sum, phenotypic changes in RBCs and decrease in hemosiderin accumulation was observed in the spleen and liver of transplanted THAL mice.

Reversal of Thalassemia Disease Phenotype in Human 13 Globin Transduced Recipient THAL Mice Recipients of [β globin gene/LCR] lentivirus-transduced bone marrow cells showed further evidence of a marked improvement in ineffective erythropoiesis. Spleen weight for B6, Thal/GFP, and Thal/Lenti-β$^{A}$-treated mice was 110, 610, and 110 mg, respectively. An increase in the number of mature RBCs was observed in the red pulp of the spleens of Thal/Lenti-v$^{A}$ mice as compared with unmanipulated THAL mice. Moreover, the mature/immature nucleated red cell ratio was reduced from 20:80 in unmanipulated Thal mice to 40:60 in Thal/Lenti-β$^{A}$ mice. These values corresponded well with the proportion of circulating normochromic normocytic red cells. The red pulp in the Lenti-β$^{A}$-treated mice was only moderately expanded, compared with the conspicuous expansion of the red pulp in control THAL mice.

Untreated THAL mice showed significant extramedullary erythropoiesis in the liver, whereas in the corrected THAL mice, extramedullary erythropoiesis was mild to moderate. No erythropoiesis was observed in the livers of normal B6 mice. Perls iron staining showed decreased iron accumulation in the recipients of [β globin gene/LCR] lentivirus transduced marrow, thus providing further evidence of reduced destruction of RBCs and improved erythropoiesis. The Perls iron staining was markedly reduced in the spleen and was negligible in the liver of the transplanted mice. In contrast, THAL mice had pronounced accumulation of hemosiderin in both the spleen and the liver. Normal B6 mice had mild hemosiderin only in the spleen, and the liver was negative.

In summary, panerythroid permanent expression of the human β globin gene was observed in all THAL mice transplanted with [β globin gene/LCR] lentivirus transduced marrow, wherein the transplanted mice exhibited an almost complete correction of all observable disease manifestations. These experiments demonstrate that a lentiviral-based vector can deliver an expression cassette for human β globin, wherein the expression of human β globin results in persistent, long-term correction of ineffective erythropoiesis and nearly complete cure of thalassemic phenotype in a mouse model for β-thalassemia. This correction was possible in the absence of preselection for transduced cells before transplantation and was associated with essentially complete reconstitution by genetically modified stem cells that resulted in stable, high-level, pancellular expression of the human β globin gene in erythroid cells. These results constitute a significant advance over results previously obtained using retroviral-based gene delivery systems.

Example VI: Construction of Self-Inactivating (SIN) Vector

Figure 7:
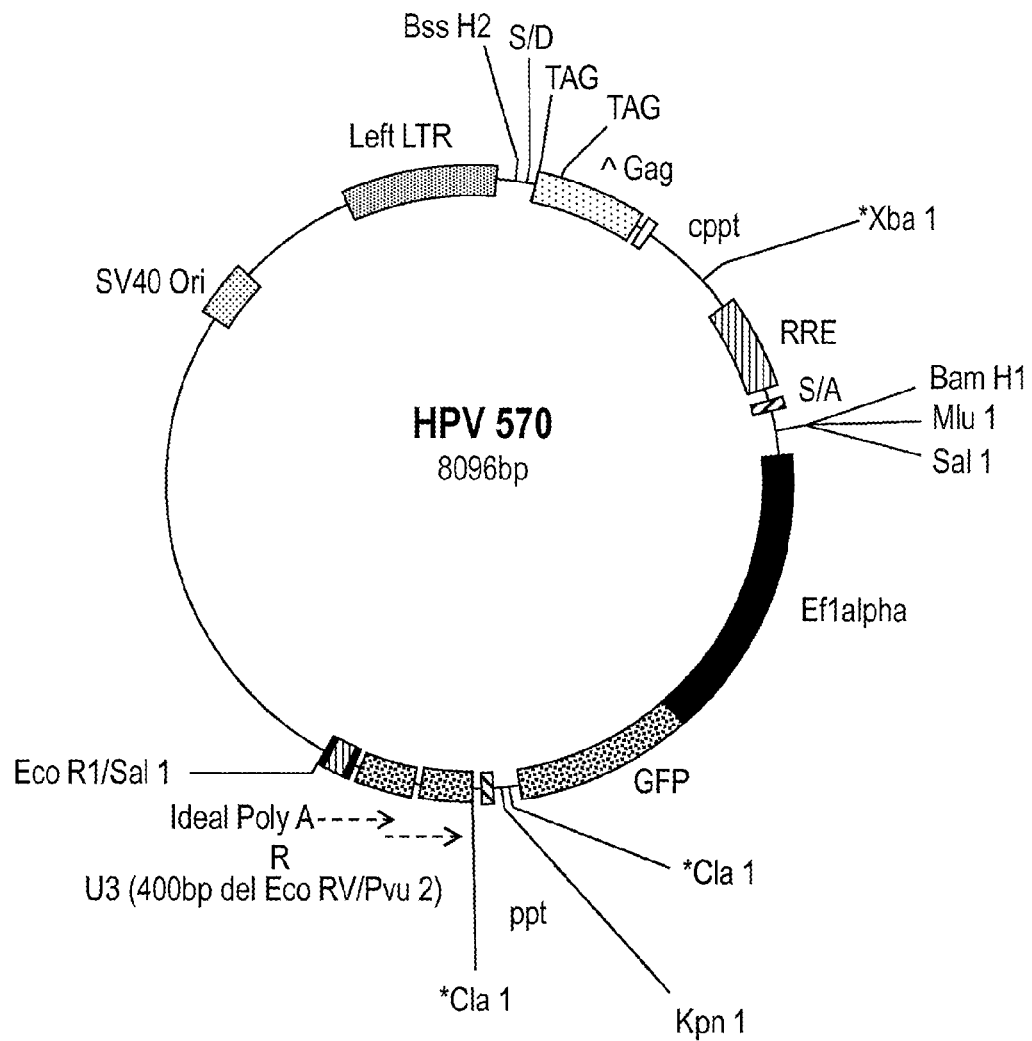
FIG. 7 graphically depicts a map of the SIN vector comprising a 399 deletion in the right LTR U3 region, which has been replaced by a doublet insulator, and a replacement in the U5 region with an ideal poly(A) sequence. The vector also contains a GFP fusion gene.
Figure 8:
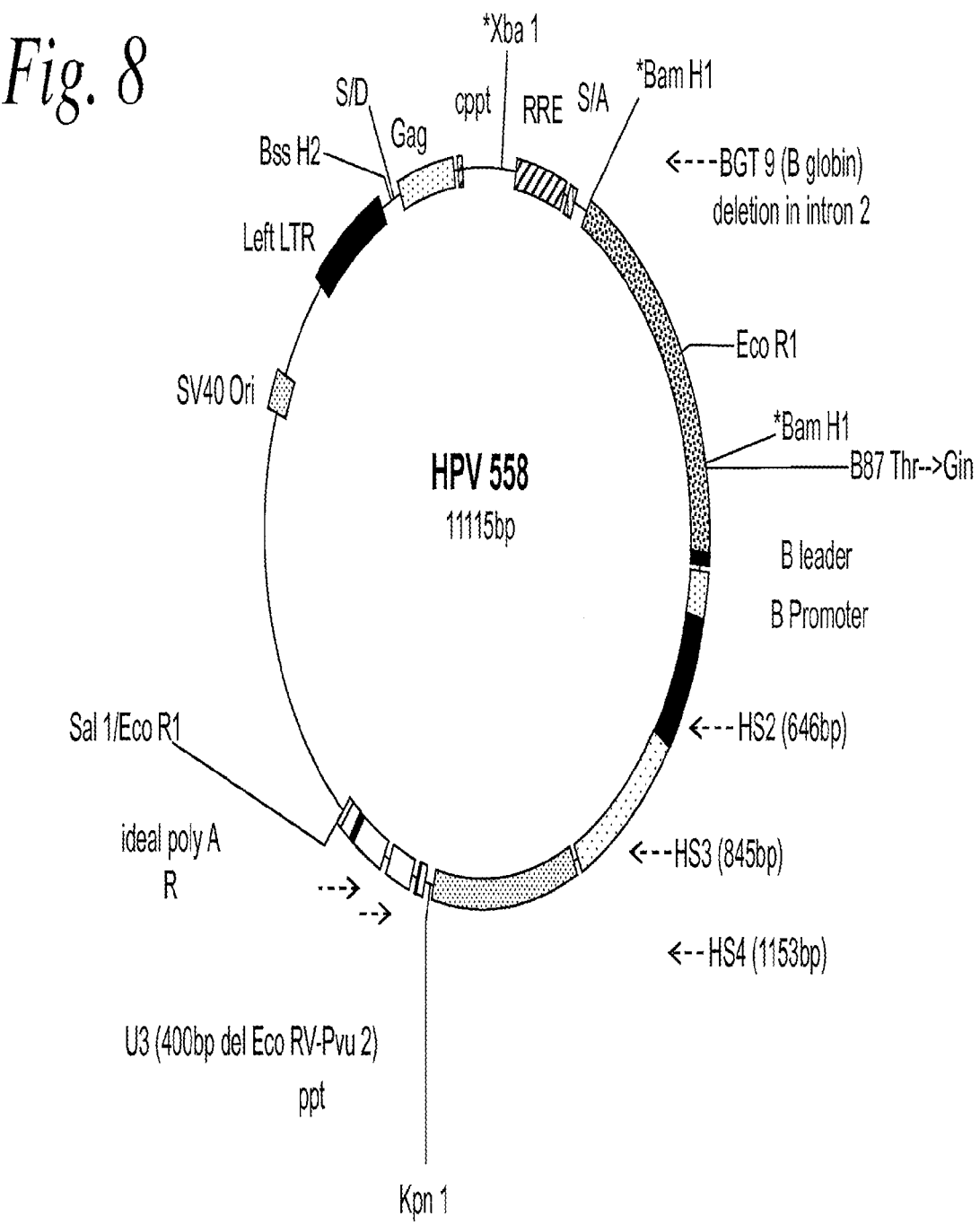
FIG. 8 graphically depicts a map of the SIN vector comprising a 399 deletion in the right LTR U3 region, which has been replaced by a doublet insulator, and a replacement in the U5 region with an ideal poly(A) sequence. This vector also contains BGT 9 (β-globin) with a deletion in intron 2.

To improve safety, the lentiviral vector described in the previous Examples was modified to include an insulator element in the right (3') LTR as follows and as shown in FIGS. 6-13. First, modifications to the 3' (right) LTR of the vector were done by subcloning the 3' LTR into a Puc19 plasmid using the Kpn 1 and Eco R1 sites, as shown in FIG. 7. A 399 by deletion was made in the U3 region of the right LTR (from the Eco RV site to the Pvu 2 site). The R region of the 3' LTR was not altered. The U5 region was replaced with an ideal polyA sequence by digesting the LTR plasmid with Hind 3 and Sal 1 (FIG. 6). This removed a small portion of the R and U5 region. This region of the R and U5 regions was replaced with the end portion of R and an ideal polyA sequence, thereby removing the U5 region without changing the R region (FIG. 6). The following oligo (OPLB 12/13) was used to achieve this replacement:

(SEQ ID NO: 1)
5'-AAGCTTGCCTTGAGTGCTTCAATGTGTGTGTTGGTTTTTTGTGT

GTCGAC-3' wherein AAGCTT is the Hind 3 restriction site, GCCTT-GAGTGCTTCA is the end of the R region, ATGTGTGT-GTTGGTTTTTTGTGTG is the poly A sequence, and GTC-GAC denotes the Sal 1 restriction site.

Figure 9:
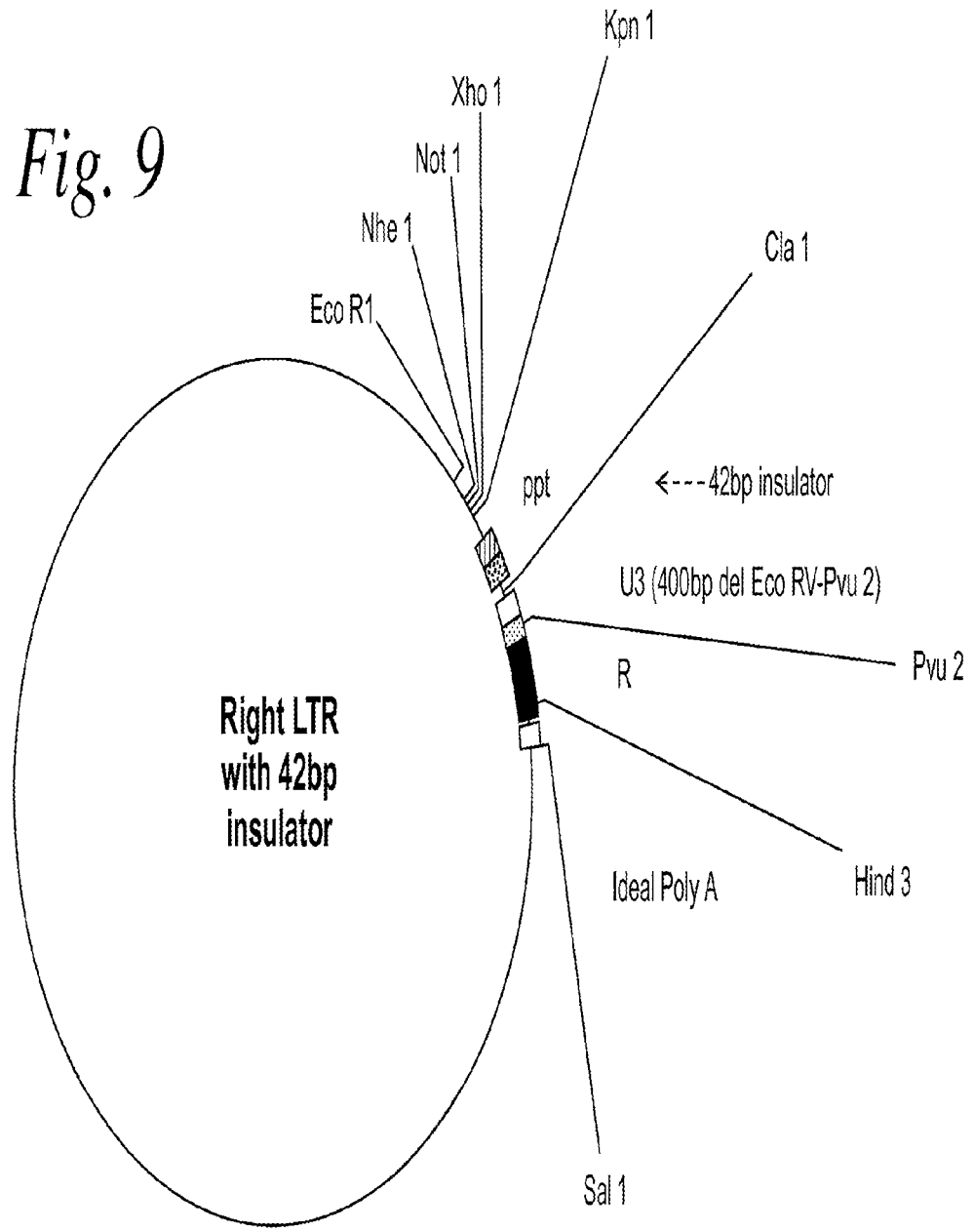
FIG. 9 graphically depicts a map of a vector comprising a right LTR with a 42 bp insulator.
Figure 10:
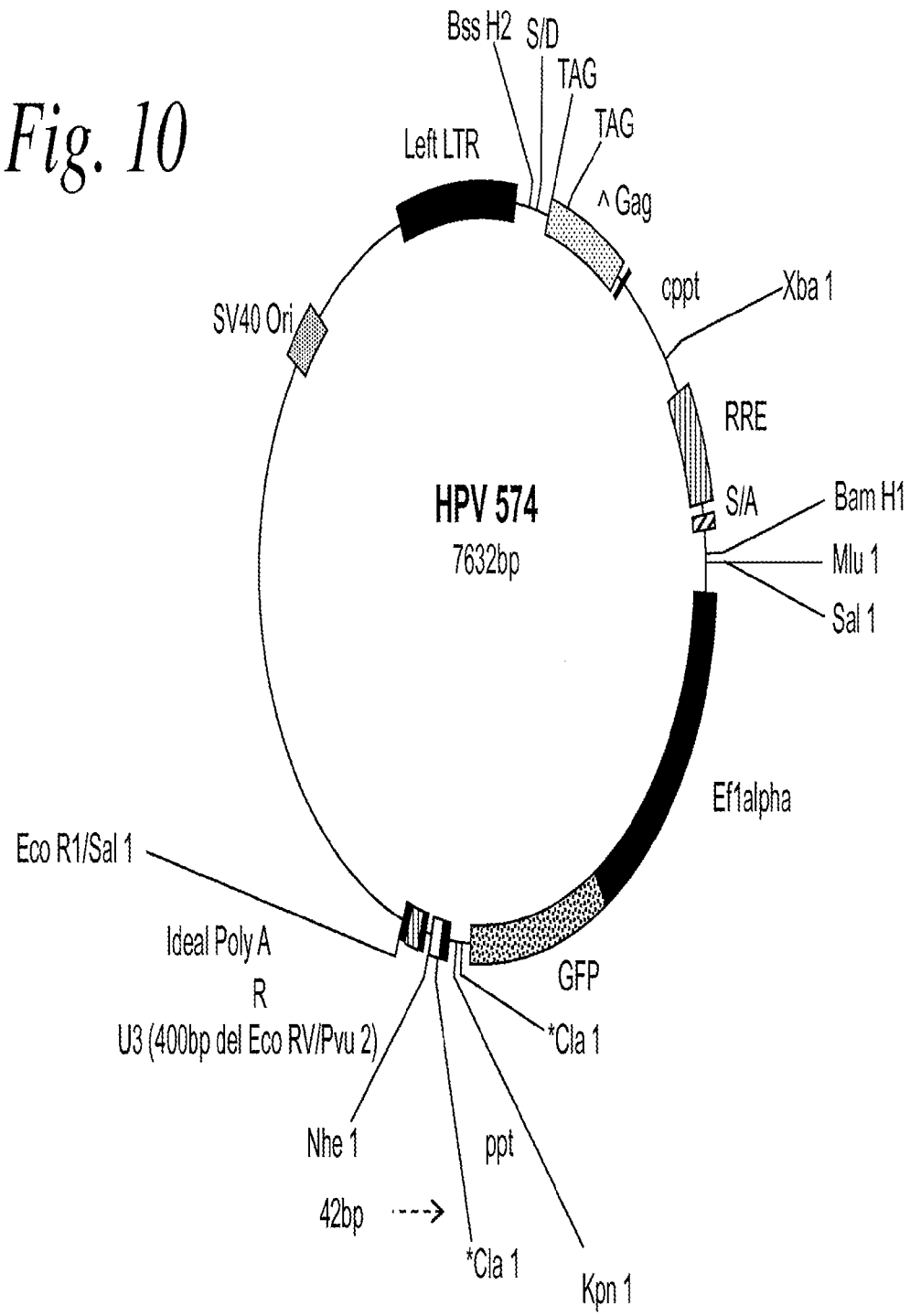
FIG. 10 graphically depicts a map of the SIN vector comprising a 399 deletion in the right LTR U3 region, which has been replaced by a 42 by insulator, and a replacement in the U5 region with an ideal poly(A) sequence. The vector also contains a GFP fusion gene.
Figure 11:
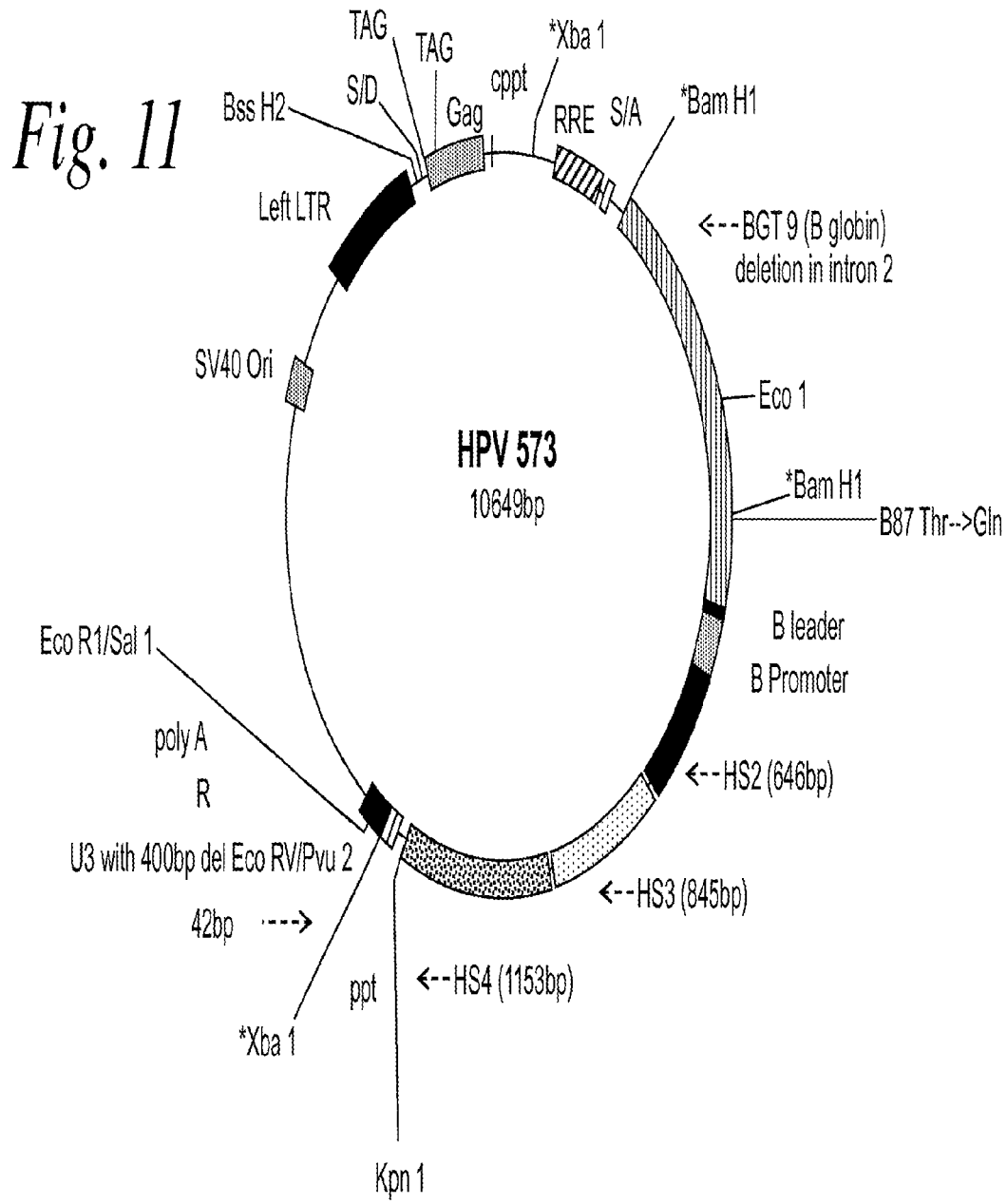
FIG. 11 graphically depicts a map of the SIN vector comprising a 399 deletion in the right LTR U3 region, which has been replaced by a 42 by insulator, and a replacement in the U5 region with an ideal poly(A) sequence. This vector also contains BGT 9 (β-globin) with a deletion in intron 2.
Figure 12:
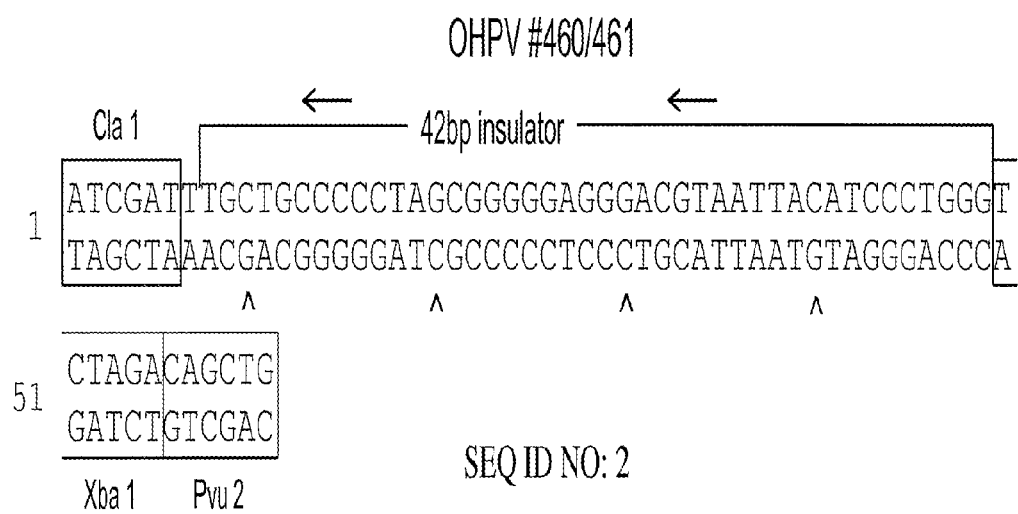
FIG. 12 shows the nucleotide sequence of oligo OHPV #460/461, including the positions of the Cla I, Xba I, and Pvu II restriction sites, and the 42 bp insulator.

SIN vectors, which contain a chicken β-Globin insulator (cHS4), were made by blunt end ligation into the EcoRV/Pvu II U3 deletion (see FIGS. 6 and 9). Examples of the insulator sequences used include a 250 bp doublet insulator (inserted into the U3 by blunting the Sal 1 and Not 1 sites) (FIG. 6), and a 42 bp version of the insulator (inserted into to U3 deletion using an oligo (OHPV 460/461) which had engineered Cla 1 and Pvu II sites) (FIG. 9). The modified 3' LTR was then inserted back into the vector using the Kpn 1 site and by blunting the EcoR1 site in the vector to the Sal 1 site from the plasmid containing the modified right LTR. Two versions of the insulated SIN vector containing either GFP or β-Globin were made (see FIGS. 7, 8, 10, and 11). Using the GFP insulated SIN vector (250 bp doublet), concentrated virus was made with a titer of $9.5 \times 10^9$ TU/ml on 3T3 cells. FIG. 13c shows that the substitution of the right U5 by a stronger poly(A) signal allows incorporation of cHS4 insulator with a minimal decrease in viral titers.

INCORPORATION BY REFERENCE

The contents of all references and patents cited herein are hereby incorporated by reference in their entirety.

EQUIVALENTS

Although the invention has been described with reference to its preferred embodiments, other embodiments can achieve the same results. Those skilled in the art will recognize or be able to ascertain using no more than routine experimentation, numerous equivalents to the specific embodiments described herein. Such equivalents are considered to be within the scope of this invention and are encompassed by the following claims.

What is claimed is:

1. A method of treating a human subject that has sickle cell disease (SCD) or β-thalassemia comprising:
   a) transducing human hematopoietic stem cells from the human subject with a self-inactivating (SIN) human immunodeficiency virus type 1 (HIV-1) lentiviral vector, wherein the lentiviral vector comprises,
      a modified 5' long terminal repeat (LTR), wherein the promoter of the modified 5' LTR is replaced with a heterologous promoter;
      an RNA export element;
      a lentiviral central polypurine tract or DNA FLAP (cPPT/FLAP) sequence;
      a β-globin promoter;
      a β-globin locus control region (LCR), wherein the β-globin promoter and β-globin LCR are operatively linked to a nucleic acid encoding a human β-globin, a human $β^{A-T87Q}$-globin or a human γ-globin; and
      a modified 3' LTR, wherein the modified 3' LTR comprises at least one deletion compared to the wild-type 3' LTR; and
   b) intravenously administering the transduced human hematopoietic stem cells to the human subject.

2. The method of claim 1, wherein the SIN lentiviral vector comprises a modified 5' LTR further comprises a deletion compared to the wild-type 5' LTR.

3. The method of claim 1, wherein the heterologous promoter of the SIN lentiviral vector is a cytomelagovirus (CMV) promoter.

4. The method of claim 1, wherein the RNA export element of the SIN lentiviral vector comprises a hepatitis B virus post-transcriptional regulatory element (PRE) or a human immunodeficiency virus (HIV) rev response element (RRE).

5. The method of claim 1, wherein the modified 3' LTR of the SIN lentiviral vector comprises a polyadenylation sequence.

6. The method of claim 1, wherein the β-globin LCR of the SIN lentiviral vector comprises DNase I hypersensitive sites 2, 3, and 4 from the human β-globin LCR.

SEQUENCE LISTING

<160> NUMBER OF SEQ ID NOS: 2

<210> SEQ ID NO 1
<211> LENGTH: 50
<212> TYPE: DNA
<213> ORGANISM: Artificial Sequence
<220> FEATURE:
<223> OTHER INFORMATION: DNA primer

<400> SEQUENCE: 1
aagcttgcct tgagtgcttc aatgtgtgtg ttggtttttt gtgtgtcgac        50

<210> SEQ ID NO 2
<211> LENGTH: 61
<212> TYPE: DNA
<213> ORGANISM: Artificial Sequence
<220> FEATURE:
<223> OTHER INFORMATION: DNA primer

<400> SEQUENCE: 2
atcgatttgc tgcccctag cgggggaggg acgtaattac atccctgggt ctagacagct        60
g                                                                      61

7. The method of claim 1, wherein the SIN lentiviral vector comprises a human β-globin 3' enhancer element.

8. The method of claim 1, wherein the SIN lentiviral vector does not comprise an insulator element.

9. The method of claim 1, wherein the SIN lentiviral vector comprises a nucleic acid cassette comprising a suicide gene operably linked to a promoter or a gene for in vivo selection of the cell.

10. The method of claim 9, wherein the suicide gene of the SIN lentiviral vector is herpes simplex virus thymidine kinase (HSV-Tk).

11. The method of claim 9, wherein the gene for in vivo selection of the SIN lentiviral vector is methylguanine methyltransferase (MGMT).

* * * * *